US011229409B2

(12) United States Patent
Deutschmann

(10) Patent No.: US 11,229,409 B2
(45) Date of Patent: Jan. 25, 2022

(54) MOBILE IMAGING RING SYSTEM

(71) Applicant: medPhoton GmbH, Salzburg (AT)

(72) Inventor: Heinrich Deutschmann, Salzburg (AT)

(73) Assignee: medPhoton GmbH, Salzburg (AT)

( * ) Notice: Subject to any disclaimer, the term of this patent is extended or adjusted under 35 U.S.C. 154(b) by 174 days.

(21) Appl. No.: 16/657,037

(22) Filed: Oct. 18, 2019

(65) Prior Publication Data

US 2020/0121267 A1 Apr. 23, 2020

Related U.S. Application Data

(60) Provisional application No. 62/747,253, filed on Oct. 18, 2018.

(30) Foreign Application Priority Data

Oct. 18, 2018 (EP) ..................................... 18201362

(51) Int. Cl.
*A61B 6/00* (2006.01)
*A61B 6/03* (2006.01)
(Continued)

(52) U.S. Cl.
CPC ................ *A61B 6/035* (2013.01); *A61B 6/08* (2013.01); *A61B 6/4078* (2013.01);
(Continued)

(58) Field of Classification Search
CPC ....... A61B 6/4405; A61B 6/08; A61B 6/4078; A61B 6/4085; A61B 6/4291; A61B 6/4476; A61B 6/547; A61B 6/56
See application file for complete search history.

(56) References Cited

U.S. PATENT DOCUMENTS

| | | | |
|---|---|---|---|
| 6,373,916 B1* | 4/2002 | Inoue ..................... | A61B 6/032 378/20 |
| 2010/0172468 A1* | 7/2010 | Gregerson ............. | A61B 6/032 378/20 |

(Continued)

FOREIGN PATENT DOCUMENTS

| | | |
|---|---|---|
| JP | 2009028160 A | 2/2009 |
| WO | 2010078481 A1 | 7/2010 |
| WO | 2017021962 A1 | 2/2017 |

OTHER PUBLICATIONS

US 5,299,248 A, 03/1994, Pelc (withdrawn)
(Continued)

*Primary Examiner* — Dani Fox
(74) *Attorney, Agent, or Firm* — Kagan Binder, PLLC

(57) ABSTRACT

The present invention provides a mobile imaging system for imaging of patients in medical interventions comprising a ring gantry with a plurality of independently rotating rings whereas a first rotating ring positions an X-ray source with collimator and a second rotating ring positions an image detector such that the region of interest (patient) can be positioned off-centered with respect to the ring center. The system supports planar X-ray imaging and Computed Tomography (CT) and Cone beam CT (CBCT) acquisitions of three dimensional (3D) volumes with variable X-ray field of views (FOVs) adapted to regions of interest (ROIs), which are not required to be of cylindrical shape. The mobile system can be equipped with stereoscopic cameras integrated in the gantry an on moving rings to support optical tracking and navigation of instruments within the same co-ordinate system of X-ray information. The gantry can be equipped with additional sensors and robotic manipulators on further rings operating in said co-ordinate system on mobile platform. The gantry provides a generic mechanical and electrical interface to a supporting structure, which can
(Continued)

be attached to a variety of mobility platforms to support robotic positioning of the system in various orientations of scanner in treatment rooms to accommodate a wide range of patient setups, including the possibility for inclined and vertical scans of patients in upright position.

19 Claims, 50 Drawing Sheets

(51) Int. Cl.
    *A61B 6/08*     (2006.01)
    *A61B 6/06*     (2006.01)
    *A61N 5/10*     (2006.01)
    *A61B 90/25*     (2016.01)
    *A61B 90/35*     (2016.01)
    *A61B 34/30*     (2016.01)
    *A61B 90/00*     (2016.01)
    *A61B 5/00*     (2006.01)
    *A61B 8/00*     (2006.01)
(52) U.S. Cl.
    CPC .......... *A61B 6/4085* (2013.01); *A61B 6/4291* (2013.01); *A61B 6/4405* (2013.01); *A61B 6/4476* (2013.01); *A61B 6/547* (2013.01); *A61B 6/56* (2013.01); *A61B 5/0062* (2013.01); *A61B 5/0077* (2013.01); *A61B 6/06* (2013.01); *A61B 6/4266* (2013.01); *A61B 6/4417* (2013.01); *A61B 8/4218* (2013.01); *A61B 34/30* (2016.02); *A61B 90/25* (2016.02); *A61B 90/35* (2016.02); *A61B 2090/366* (2016.02); *A61N 2005/1061* (2013.01)

(56) References Cited

U.S. PATENT DOCUMENTS

2012/0324648 A1   12/2012   Amano
2013/0243151 A1    9/2013   Shih
2014/0046212 A1*   2/2014   Deutschmann ...... A61B 6/4452
                                                                    600/567

OTHER PUBLICATIONS

Extended European Search Report for European Application No. 19202618.5, dated Aug. 12, 2020 (16 pages).
E-Space English Abstract for JP 2009028160.

* cited by examiner

MOBILE IMAGING RING SYSTEM

This application claims priority to U.S. Provisional Patent Application No. 62/747,253 entitled. "MOBILE IMAGING RING SYSTEM," filed on Oct. 18, 2018; and also claims priority to EP Patent Application No. 18201362.3 entitled "MOBILE IMAGING RING SYSTEM," filed on Oct. 18, 2018; the contents of both of which are hereby incorporated by reference.

The present invention relates to a mobile imaging ring system comprising a ring shaped gantry with independently rotating outer rings to position arms, whereby one first arm carries an X-ray source with collimator and one second arm carries an X-ray image detector. The system can be used for planar X-ray imaging or volumetric scans in Computed Tomograpy (CT) with fan beams or cone beams (CBCT). The gantry has a very large bore diameter but a small foot print, it is simultaneously slim in outer diameter and length and light to accommodate flexible imaging of patients in various setups and scenarios as required during medical interventions, such as radiation therapy or surgery in tight situations with limited space in operating rooms (ORs). These properties, which are achieved by the ring gantry's special design, are an advantage in comparison with prior art conventional medical CT units, which are bulkier, heavier and limited in bore size, mobility, flexibility and applications. For example in brachytherapy of gynecological or rectal cancer, with the patient oriented in feet first supine (FFS) orientation towards the gantry, the system's slim form factor and large bore opens space for the therapist and gives access to patient and applicators from the backside of the gantry, which is hardly possible with closed CT-gantries. In comparison with mobile C-arms or O-arms, the closed ring geometry provides a rigid and stiff structure, which is essential for highest accuracy and spatial resolution of reconstructed volumes.

The invention is defined by the independent claims; the dependent claims define embodiments of the invention.

Specifically, the invention provides a mobile imaging ring system comprising a gantry shaped in a closed ring form. The gantry comprises an inner ring, a central stationary ring, a source ring arranged on one side of and configured to be independently rotatable along the central stationary ring, wherein a radiation source is mounted on the source ring so that the radiation source is rotatable around the gantry by rotating the source ring, and a detector ring arranged on the other side of and configured to be independently rotatable along the central stationary ring, wherein a radiation detector is mounted on the detector ring so that the radiation detector is rotatable around the gantry by rotating the detector ring. The central stationary ring, the source ring and the detector ring are provided on the outer surface of the inner ring. The System further comprises a supporting structure carrying the ring shaped gantry, the gantry being mounted to the supporting structure such that a plane defined by the ring shape of the gantry is tiltable relative to the supporting structure.

Preferably, the detector and the source are mounted on the detector and source rings, respectively, in such a way that their movements do not interfere with each other and with the supporting structure when independently rotating the detector and source rings around the entire circumference of the gantry.

Each of the rotatable detector and source rings may further be assembled with the stationary central ring using a ball bearing. The rotatable rings preferably are gearwheel rings matching a circulating tooth belt driven by a toothed pinion on a motor.

The source and/or the detector may be held by source and detector arms mounted to the source and detector rings, respectively, wherein the source arm extends to one side of the gantry and the detector arm extends to the side of the gantry opposite to the side where the source arm extends. The source and/or detector arms are preferably folded to the inner bore of the gantry allowing the detector to be positioned on the same side of the gantry as the source and opposite to the source or at any offset angle from the opposing position, up to and including 180°.

The supporting structure may house a power supply such as a battery, drive controls, inverter components, a controller for signal processing, and/or a computer for image processing. Preferably, the gantry may be a universal gantry that preferably has a generic mechanical interface and a generic electrical interface to the supporting structure. The universal gantry thus may be combined with a variety of mobility platforms by disconnecting/connecting the mechanical junction and the electrical cables, e.g. power and signal cables, running between gantry and alternative supporting structures. The electrical connection between the detector and source with electrical components housed in the supporting structure may be provided via flat cables inserted into the gantry, wherein the length of the flat cables preferably corresponds at least to the circumference of the gantry in order to allow in minimum one full rotation of the detector and source rings.

The supporting structure may comprise at least two legs allowing the supporting structure to stand on the floor or being attached to a carriage on rails. Each leg may have a, preferably motorized, hip joint in connection with the supporting structure, thereby allowing tilting the gantry such that the plane defined by the ring shape of the gantry in a minimal range from −90° to 90° relative to the supporting structure.

The supporting structure may comprise stabilizing means for establishing a stable position of the system when standing on the floor. This may by preferably be achieved using load sensors.

The supporting structure may further comprise moving means for allowing a controlled movement of the system. Preferably, the moving means comprises wheels, preferably motorized wheels, or a robotic quadrupod or hexapod.

The system may further comprise a tracking system for determining the position and orientation of the gantry relative to a room coordinate system.

At least one additional rotatable ring may further be arranged on the gantry. The additional ring may be mounted with a robotic arm for holding additional instruments such as a sonographic sensor, a surface scanner, a second detector, a second source, a camera, a video projector, a light source, a microscope, or tools for assisting in or actively performing image guided robotic surgery or image guided radiation therapy.

The system may further comprise a movable laser system on the detector arm. The laser system may comprise four independently moving and pivoting and switchable line lasers mounted on four carriages on rails parallel to the detector's active area. The planes defined by the line lasers may thus track the independently rotating source and/or collimator jaws to project a cross hair of the X-ray field or the adjusted field of view onto the exit skin of the patient.

The system may further comprise cameras mounted to the inner ring and/or the detector arm and/or the source arm and/or the supporting structure and/or the hand held controls. The cameras may be used to provide geometrical tracking information about patient, instruments and/or room in the ring based, mobile imaging coordinate system for navigation of instruments and/or the imaging system's moveable components. This may include positioning of line lasers and source and detector and jaws and robotic arms as well as the movable imaging system itself.

The present invention further provides an independent, room mounted rail structure with adjustable inclination relative to floor with carriage and docking means to dock and move the system according to the present invention for imaging in vertical, inclined or horizontal positions.

Moreover, the present invention provides a filter wheel, synchronously rotating with periodically emitted X-ray pulses from a single source X-ray source, such that a first low energy X-ray pulse passes a first sector and a second high energy X-ray pulse passes an opposing sector on the wheel, with the filter wheel having an air insert at first sector and a beam hardening filtration at the opposing sector for enhanced dual energy imaging. The filter wheel may preferably used with the system of the present invention, such as with the radiation source mounted on the source ring of the mobile imaging ring system. Alternatively or additionally, the filter wheel may have a first sector insert comprising a plurality of concentrically aligned, ring shaped blockers with air spacers and a second sector insert comprising same plurality of circular ring shaped blockers with concentric ring shaped air spacers, whereas the second sector's rings are phase shifted such that after every first pulse is blocked and every second pulse is open for the X-ray beam for object scatter removal.

The present invention moreover provides an anti-scatter line grid to remove object scatter from primary X-ray beams, which is movable over the active area of a flat panel detector in Cone Beam Computed Tomography with a sufficiently large in size to accommodate collimated fan beams to essentially perform a CT and can be retracted to perform a CBCT. The anti-scatter line grid may preferably be used with the mobile imaging ring system of the present invention, e.g. in conjunction with the radiation detector mounted on the detector ring.

In the following, various aspects of the present invention are described in more detail.

Extending Arms

For the present invention, during imaging, the patient's region of interest (ROI) is located essentially in front and inside the ring gantry with the arms of the system's X-ray source and detector extending in a direction longitudinally in front of the ring, parallel to the ring's symmetry axis. Arms are rotating along the circumference of the ring gantry. The inner, front and backside of the ring gantry are not rotating. The outer surface of the ring gantry has one centrally located stationary ring, which provides stiffness and mechanical and electrical interfaces to a supporting structure, the mobility platform. Next to this stationary ring, at both sides, at least two rotating rings, the source ring and the detector ring, are mounted to the ring gantry to move the source arm and the detector arm independently. The X-ray source arm extends to the front side of the ring gantry such that the X-ray source is effectively rotating in front of the gantry. The detector arm extends from the detector ring to the backside of the ring gantry to enable full rotation of ring and arm with no interference with the supporting structure attached to the stationary ring. In order to position the image detector opposite to the X-ray source in front of the ring gantry, the detector arm is folded at the backside of the ring gantry to the inner bore such that the detector, which is an amorphous silicon flat panel detector in one embodiment of the present invention, effectively rotates inside and in front of the ring gantry, leaving a small gap between detector arm and ring and source arm as well. By this arrangement, it is possible to move the source over the detector, enabling a compact system parking position with source and detector arms positioned at same gantry angle. For applications in external beam radiation therapy, where imaging is required during beam delivery in the treatment room's isocenter position, or for applications in image guided medical interventions, where the patient and manipulated instruments need to be imaged in the ROI while space is required for surgeons and manipulators, the extended distance of the ring gantry to the ROI is beneficial and advantageous compared to prior art: Conventional CT units or O-arm systems or C-arms leave less space for the medical team at least at one side of the operating room (OR) table, if in place for imaging, and it is not possible to have source and detector simultaneously parked underneath the surgical table.

Arms can be detached from rotating rings for servicing or exchange with functionality of different arm, for example, if two detectors need to be installed for PET imaging.

Gantry Design

For each of the independently rotating rings, a precise large diameter ball bearing is assembled with a stationary inner ring (the gantry) and a rotating outer ring, which is a gearwheel ring matching a circulating tooth belt which is driven by a toothed pinion on motor below the gantry. The arms are connected to gearwheel rings and independently driven by the belt drives, the motors have brakes and encoders or resolvers to determine the position of the arm in control loops of the motion control system, motor currents are sensed in order to detect collisions. The equipment on the arms, for example the X-ray source and collimator on the source arm or a flat panel on the detector arm, are powered and signals are wired via a cable system, which consists of flexible and durable flat cables with low bending radii. The cables are inserted into the gantry in horizontal scan position from below, where the drive units and supporting structure are located. From the point of insertion, the flat cables use the full space between the inner, stationary gantry ring and an outer, rotating ring until they are fixed to the respective arm and guided to the equipment on the arm. Because of the limited length of cables, the maximum travel range of arms is limited from a minimum to a maximum position.

In one embodiment of the present invention, the length of cables is limited to less than one time the circumference of the ring. In such embodiment, the arm can only rotate a maximum distance of less than two turns with the cable loop rotating less than one turn, thus leaving some space for cable insertion and extraction. In this case, a cable retraction mechanism, which forces the cable loop to a defined position with respect to arm and gantry can be realized, either by (a) a constant force spring roller which constantly pulls the cable loop via an idler pulley towards a home position or by (b) a belt, which is attached to the rotating arm opposite to the cable extraction, going to said idler pulley at cable loop and back to an endpoint fixation on the stationary gantry ring, keeping the cable loop constantly in place at half angle of outer ring and arm.

In another embodiment of the present invention, the flat cables are longer to allow for a larger range of rotations, i.e. four turns possible per arm, which is beneficial for helical scan CT acquisitions with the source surrounding the patient four times, providing a longitudinal FOV of a multiple of the length of a collimated fan beam. In such an embodiment, the length of cables must be two times the circumference of the ring, which is possible with two layers of flat cables in the space between inner stationary ring gantry and outer rotating ring with arm. In this case, no simple cable retraction mechanism is possible and the cable loop is only guided by friction between cables and rings, requiring a certain stiffness of the cable bundle at the bending in the loop. Similar to the concept of the belt pulling the idler pulley described above, in another embodiment of the invention, two ropes could be deployed to idler pulleys left and right side of the flat cables. By such means, the cable loop can be kept constantly in place at half angle of outer ring and arm, however, the room for ropes must be separated from room of cables, leading to a slightly longer gantry construction.

In another embodiment of the present invention, the rotating rings can be connected with the stationary inner ring with a slip ring for power and signals to arms.

The gantry is designed to provide a generic mechanical and electrical interface to a supporting structure. In one simple embodiment of the present invention, the gantry can be mounted stationary in horizontal position for lying patients on beds with longitudinally movable couchtops, like in prior art CT. In another embodiment, the gantry may be attached in vertical position on vertical rails in order to scan seated patients or patients in upright position, which may be relevant in orthopedic use-cases (imaging of spine, hips, knee under load) or in seated position, which may be relevant in particle therapy (imaging during eye treatments). In another embodiment of the present invention, the gantry may be directly attached to horizontally oriented rails on the ceiling in order to enable scanning of lying patients on stationary beds, for example in proton therapy, where patients are often aligned with respect to a treatment beam's isocenter with robotic patient positioning systems.

The gantry's inner structure must be stiff for highest spatial resolution in imaging and light for mobility. This can be realized utilizing compound material, e.g. an aluminum honeycomb sandwich construction for the inner, stationary gantry ring and also for the central space between inner ring and stationary outer ring. In the present invention, the front and backside of the ring gantry can be dismantled by means of a bayonet lock, providing easy access to the cable management system.

Tilt

In a preferred embodiment of the present invention, the gantry is rigidly attached to a supporting structure which resembles a mobility platform. The supporting structure is essentially as slim as the gantry in longitudinal direction and shall not extend the gantry's front surface, in order to allow free rotation of X-ray arm with source and collimator in front of it, and it provides space in form of a circular gap at front side and backside for arms to be rotated. The supporting structure attaches to the stationary, non-rotating ring at the outer side of the gantry, is typically located below the gantry if in horizontal scan position, but would leave sufficient space and distance to the floor in order not to collide with base of OR tables if in front position during imaging. The supporting structure provides space for power supplies, batteries, drive controls, X-ray inverter components, programmable logic controller (PLC) for signal processing and a built-in computer for image processing and applications with user interface and moves with the gantry.

In one embodiment of the present invention, the supporting structure is connected with two legs at each side to carry the complete system. Each leg has a motorized hip joint in connection with the supporting structure, allowing to tilt the gantry in a range essentially equivalent to +/−90° with both legs on the floor. This is intended to be used for vertical scan applications, servicing, stepping maneuvers and to reduce the package size of the system in crating and shipment. The legs are inclined between hip joint and heel on floor in order to allow unconstrained rotation of source even with the gantry tilted top forward by −30°, for example. Both legs have wheels at bottom in the sole, one wheel at toes, one wheel at heel. In the effect, the system stands on four points on the floor, on two legs, which can be tilted independently at the hip joints. It is essential in precise imaging applications, that no instabilities or vibrations may cause the gantry to move unexpectedly during a scan, and it is important to have all four wheels on the floor, even if a hospital environment provides an uneven floor or if a potential dirtying sticks to a wheel. For this purpose, the present invention accommodates load sensors, one in the left leg and one in the right leg, to measure the forces applied at the toes. If the force at left toe differs significantly from force at right toe, it can be concluded that the system is not stabilized. The load sensor signals are processed in the PLC and hip joints are rotated to counterbalance the legs until a stable position is reached for imaging. Alternatively, in another embodiment of the present invention, if no self-locking worm drives or spiral drives or similar are used in gear boxes at hip joints, but harmonic drives or cycloid drives which can be operated reversely, the motor currents at both hip joints can be sensed and compared between left and right leg to establish a stable position.

Mobility

Although the four wheels mentioned above can simply be passive caster wheels or fixed rotating wheels to allow manual positioning of the system, in a preferred embodiment of the present invention, the wheels at heels are motorized and actively driven and steered and wheels at toes are actively steered as well. By adjusting the steering angle of all four wheels being parallel in a certain direction, the system would move on the floor in the adjusted direction, forward or backward, longitudinally, laterally or any other angle of choice. Prior art mobile CT units allow similarly a free positioning of the CT unit by motorized Omni-wheels or Mecanum-wheels. However, in sterile OR cleaning of such wheels is difficult and precision of conventional wheels with crowned rubber tires is higher, as required for such imaging applications: Rotations on floor about any adjustable center point, for example the imaging center of the X-ray system, can be performed by adjusting the steering angle of all four wheels to be essentially tangential on concentric circles around the center point of rotation. The rotation is initiated by activating the drive units in left and right heel of legs with an independent speed of rotation, which is proportional to the radius of the circle around the center point of rotation, the path along the wheels would drive during rotation of system on floor. Motion along any trajectory can be performed in different modes, for example in a self-parallel mode, whereby the system is moved parallel to itself at all points along a specified path (which is a use-case in the OR when moving the system from a parking position to an imaging position) or in a tangential mode, whereby the system is moved tangentially along a specified path, maintaining its orientation relative to the path, similar to cars on roads, which normally have front wheels in front of the car in driving direction. Any other combined motion on floor can also be realized, which makes up an essentially robotic appearance with simultaneous motion of wheels on floor synchronized with motion of gantry tilt, source arm, collimator jaws, detector arm and optional other arms on rings on gantry, orchestrated via the motion control system. By such means, the imaging system can be driven manually, using a human machine interface (HMI), for example buttons to enable motion or joysticks or a hand-pendant or console or a touch screen or augmented reality glasses to navigate the system in jog mode for ad-hoc motion. It is also possible to teach the robotic system to execute preplanned motion along trajectories, for example to move from a trained parking position to an imaging position. In a preferred embodiment of the present invention, it is possible for the user to specify an imaging center and a desired direction of a planar projection in 3D space, for example during surgery with a patient in situ. The robotic system would then calculate the inverse kinematics and allows the user to move all components, source, detector, gantry tilt, legs synchronously and directly to the desired imaging position by means of a button click.

Adaptive Trajectories

The present invention uses independent rotation of X-ray source and detector arms for flexible, adaptive FOVs. Unlike prior art CT, CBCT, O-arm or C-arm systems, where the 3D FOV is typically cylindrically shaped and the patient needs to be centered in the isocenter between source and detector, the described ring gantry allows for non-isocentric image acquisitions of irregularly shaped FOVs, such that the ROI can be placed anywhere inside the bore and can have any convex shape. This is advantageous, because it is no longer required to adjust the pose, height and lateral position of the patient between the medical intervention and the imaging sequence. In one embodiment of the present invention, this is realized by definition of an imaging center inside the ROI, which may be offset from the ring center. By making this imaging center the virtual axis of rotation for source and detector, effectively varying the speed of rotation of source (and detector) along the ring gantry, such that a ray from the focal spot through the imaging center rotates by equidistant angles per time interval. By such approach, the distribution of photons in the ROI would be essentially equivalent to a prior art CBCT and sufficient for high quality image reconstruction of off-centered ROIs. Technically, this can be achieved by dynamic collimation, i.e. motion of four independent X-ray collimator jaws during rotation of source and detector, to track the predefined ROI, together with continuous adjustment of the detector offset angle. During a rotation of the source, the distance between focus and imaging center may also vary for off-centered ROIs and so will the projected shape and magnification of the ROI to the detector change from angle to angle. For large objects and FOVs (LFOV) with detectors of limited active area or circumference, this can be taken into account during full scans) (>=360° by setting the position of the detector relative to source and (off-centered) ROI such that the border of the ROI is projected to the border of the detector's active area for every gantry angle, while the X-ray beam is collimated in a trans-axial view to the same border on one side and to the imaging center (with some overlap) on the other side. This would result in highly dynamic, synchronized motion trajectories for source, detector and collimator jaws in adaptive FOV acquisitions and allows reconstruction of limited and enlarged FOVs with minimum dose to the patient, no unnecessarily exposure of tissue with X-rays outside the ROI, reduced production of scattered radiation in object to be scanned and therefore improved image quality in CT and CBCT.

Prior art CBCT effectively uses a constant offset between source and detector during image acquisitions (zero offset for small circular FOV (SFOV) or predetermined offset used for large circular FOV (LFOV) acquisitions). By means of a motion control system which allows to synchronize the free motion of individual axes, the present invention supports variable speed of source and detector during an X-ray exposure and dynamic collimation of the X-ray beam to (a) expose the active area of the panel only, independent of its relative position to the primary X-ray cone and (b) to irradiate a limited ROI inside the object, which is neither necessarily located in the center of the ring gantry nor necessarily shaped circular in a trans-axial view. While (a) is required for regulatory reasons in medical devices (no ionizing X-rays shall penetrate the patient if not captured by the detector), (b) is useful to reduce the dose to the patient if smaller ROIs are to be imaged. Collimation to limited FOVs, i.e. the target volume for cancer treatment in radiation therapy helps to reduce the amount of scatter generated in the object and thus improves image quality and soft tissue contrast in CBCT. Adaptive collimation to the body outline helps to reduce the amount of un-attenuated radiation through air reaching the detector.

Helical Trajectories

The present invention can be used to acquire helical CT scans with an accordingly collimated cone beam (to form the shape of a fan beam, i.e. a narrow slit) rotating along a helical trajectory, with the wheels on legs moving the system slowly forward or backward during exposure and acquisition. In prior art CT (on rails), the accuracy of the longitudinal motion (pitch) of patient couch (or system) is crucial for accurate and artifact-free reconstruction of volumes in helical scans. In the present invention, the accuracy is achieved despite potentially uneven floors by means of (a) tracking the gantry with markers attached thereto by an external tracking system during the acquisition, such that the location and orientation of the gantry is precisely known for every image frame read from the detector or (b) tracking texture in the floor by means of cameras located in the legs in order to derive the system's relative position on floor and combining this information with signals from load sensors and built-in inclinometers, such that the location of the gantry is known for every frame or (c) analysis of the resulting sinogram, i.e. the stack of acquired projections, for subsequent low pass filtering of irregularities of motion and correction of system position in longitudinal direction.

Circular Trajectory

Because of the complexity of corrections of errors in free floating helical scans, due to potentially irregular motion of the system on imperfect floor and residual errors, which might degrade image quality and affect the system's overall geometrical accuracy, an alternative trajectory is the classical circular trajectory in CBCT. In the present invention, the system's ability to rotate four full rotations can be exploited to acquire a subsequent series of fan beam acquisitions, effectively splitting the large field size of an open CBCT FOV into four fan beams. Similar to helical CT, the four fan beam acquisitions would come with significantly reduced object scatter and partial scans can be reconstructed with increased HU accuracy. The partially reconstructed volumes may be stitched together in 3D to form one CT of the complete FOV. Acquisition and reconstruction is done on regular circular trajectories, whereby the circles can (a) be parallel shifted in longitudinal direction if the system is moved between the single fan beam scans on floor or (b) have the same plane with no motion on floor required, if the collimator is used to shift the fan beam in longitudinal direction.

Short Scan Trajectory

The present invention can be used for acquiring short-scan small FOV CBCTs where x-ray data are acquired and back-projected while a source rotation around the imaged object's center of (180 plus the average cone angle determined by the applied x-ray beam's divergence) degrees in either clockwise or counter-clockwise rotation direction is performed.

The required effective source rotation arc measured in the machine's coordinate depends on the localization of the imaged object's center. The invention allows for dynamic fade-in collimation at the beginning or fade-out collimation at the end of the short-scan trajectory collimation in order to physically avoid x-ray emission to the imaged object and detector where the data redundancy weighting during reconstruction would eliminate the sensed dose. This contributes to dose saving to the imaged object.

Dual Short Scan Trajectory

The present invention can be used for acquiring dual short-scan large FOV CBCTs which is composed of two subsequent short-scan trajectories which have with modified relative source to detector offset. The size of the FOV is determined by the outer projection lines between source and detector edge of both trajectories. The volumes of two subsequent short-scans can either be composed in 3D to form a large FOV CBCT or inline (i.e. incrementally in real-time) reconstructed by modified redundancy weighting. This scan type can be combined with dynamic collimation fade-in or fade-out technique as described for short-scan for saving dose to the imaged object.

Ultralarge FOV

In prior art CBCT, the maximum lateral field size is not only a function of X-ray cone angle and geometry, but also of detector size. Common flat panel detector reach sizes of up to 43 cm resulting in lateral field of views of not more than 25 cm, depending on the systems geometry. In a large field of view (LFOV) setup with shifted detector, this can go up to field sizes of up to 50 cm. In one embodiment of the present invention we propose an ultra LFOV protocol that combines a regular LFOV protocol with a second full rotation that covers only the outer parts of the radial FOV in the form of a donut. This enables lateral field of view sizes so large that they are only limited by the circumference of the arms. This type of protocol shall not be limited to combine 2 acquisitions but to combine and merge multiple acquisitions with increasing inner and outer diameter.

Saddle Trajectories

In one embodiment of the present invention, saddle trajectories can be executed in order to move the source during rotation along the gantry's circumference longitudinally forward and backward in an oscillating fashion by means of adjusting the gantry tilt angle, without any motion of system leg's on floor. Saddle trajectories are known to reduce cone beam artefacts in comparison to circular trajectories, providing an isotropic modulation transfer function not only at the trans-axially located central slice, but also in superior and inferior regions of the FOV. A practical implication of saddle trajectories with the present invention is the ability to avoid collisions of the rotating source with OR table columns when the system is in a longitudinally foremost position, such that the oscillation of source in longitudinal direction is preplanned and optimized in way to spare the area of the column. For accurate image reconstruction, inclinometers are mounted on gantry or supporting structure, to provide redundantly accurate information about the orientation of the gantry during a scan in real time for each frame of projection.

Vertical/Inclined/Horizontal Scans

In one embodiment of the present invention, the mobile imaging system can be docked to a carriage on rails at an elevator, for example at docking points at the inner side of the legs, at the supporting structure or at the pivoting axes of the hip joints. The elevator can lift the imaging system and the gantry can be tilted to accommodate vertical scans, supported by the carriage on rails, for scans of patients in upright position or seated chair treatments. The carriage on rails of the elevator can be positioned precisely at any point alongside of the elevator's rails and be used to generate a precise feed during helical scans (pitch), if synchronized with the imaging system's motion control system. In one embodiment of the present invention, the inclination of the elevator and rails with respect to floor is adjustable: The rails can be oriented essentially in a vertical direction (attached to a wall) for vertical scans or oblique (for seated chair treatments with inclined rest of seat) or in a substantially horizontal position for scans of lying patients on a bed. The mechanical precision of rails is superior to potentially uneven and dirty floors in a general hospital environment, so helical scans in horizontal position may be performed more precisely with the ring docked to the carriage on rails compared to free floating on floor. One advantage of the described invention is that the rails are essentially a low cost mechanical structure which can be manufactured rather radiation hard and installed in rooms where higher doses of scattered neutrons is to be expected, likely to damage expensive imaging equipment, for example in boron neutron capture therapy (BNCT) or ion beam therapy with particles (protons, carbon ions). In such scenarios, the mobile imaging ring may be used in preparation of patient after setup in treatment position, but moved out of the radiation area during patient treatment.

Sterility

The inner, front and back surfaces of the ring gantry are moveable with the system but stationary during normal scans, such that areas in proximity or above the patient can be kept clean (aseptic) or covered (sterile) during operations or interventions. During normal imaging procedures in an OR with the patient and ring axis in a horizontal orientation, the X-ray source will move in potentially contaminated zones below the patient, in the lower 180° along the rings' circumference, and will become non-sterile. For such acquisitions, the gantry and the detector may be covered with a sterile coating in the upper 180° of the circumference. The detector will then be allowed to move above the patient, opposite to the source, to capture images of the patient, sufficient for full three dimensional (3D) CBCT image reconstruction inline to short scan trajectory acquisitions (180° rotation+X-ray beam divergency angle), never entering prohibited, potentially contaminated areas. The gap between detector arm and gantry bore can also be used to insert a thin-walled pipe attached to the gantry, effectively creating a tunnel and separating a cylindrical volume inside of the bore diameter, where the detector rotates, from the space outside, where the source rotates. If the tunnel extends from the gantry at least as long as the source arm, then the non-sterile source can also rotate above the patient in a surgical setting, shielded by the tunnel wall. The tunnel can be manufactured from thin, radio-transparent foils of polycarbonate or similar plastics which can be rolled up and packed in tubes of smaller diameters for sterilizing and storage. The foils can then be unrolled and attached to the bore of the gantry in preparation of the surgical maneuver.

Draping

In state of the art, the draping procedures for imaging equipment in sterile OR environments have to be carried out manually and are often very time consuming and prone to failure. For the present invention, a draping concept is presented which provides a sterile gantry and sterile detector arm and a shielding tunnel for the source arm ready for imaging in a semiautomatic way. For this purpose, a sterile, form-fitting drape bag simply needs to be pulled over the detector arm at a specified gantry angle, inserted into the gap between gantry bore and arm and fixed outside at the rear end of the detector arm. Alongside of this drape bag, a roller of a radio-transparent, sterile foil is preliminary and temporarily attached directly thereto with tape in order to prevent cross-contamination of the detector drape and the tunnel to be built up from the foil during the draping procedure. The roller will then be loosely attached to the detector arm such that it can roll and the open end of the rolled up foil will be attached to the bore of the gantry. Now, the temporal connection between the detector drape and the roller will be loosed, tape removed. The detector arm is now free to rotate and can be moved from the predefined start to a stop position, unrolling the foil, by such creating a tunnel as sterile barrier. At the stop position, the second end of the foil needs to be attached to the bore of the gantry as well. Depending on the foil material and stiffness, intermediate fixations may be placed at the gantry, either (double sided) adhesive tape or magnetic fixes or form-fitting clips to secure the foil inside the bore.

Tunnel

In the present embodiment, the tunnel described above can also be used as protecting means to prevent hazard to the patient in case the system is operated in a mode with fast source rotations. This is an advantage in comparison with state of the art open CBCT systems, where the moving X-ray source creates is a potential risk of collision with the patient. As a risk mitigation, conventional open CBCT systems are either limited in speed or require patient fixation.

The thin-walled, radio-transparent tunnel between circular paths of source and detector can also be used as a carrying structure for small, radio-opaque blocker structures to be attached thereto creating a pattern which can be used to modulate the primary X-ray radiation, which penetrates the object to be scanned (i.e. the patient). The so modulated primary radiation will be attenuated by the object, physically by interaction of X-rays with matter by photo-absorption or Compton- or coherent scatter. All scattered photons which reach the detector contribute to image degration, thus methods must be applied to subtract scatter from primary. If the pattern of blocker structures attenuates the primary spectrum sufficiently (e.g. 3 mm of led attenuate more than 99% of 120 kVp X-ray photons), then the primary modulation can be described as a binary stopping array (BSA), where detector pixels behind a blocker measure scattered radiation only. This information can be used to estimate the scatter distribution between the blocker structures and to subtract scatter contributions from the acquired projection images for enhanced 3D image quality.

OR Table Compatibility

The present invention can be used in combination with any OR table with radio-transparent couch. In spine surgery, Jackson tables are commonly used, where the patient is positioned on a couch which is carried by two vertical columns at superior and inferior end of the couch, the couch can be disconnected from the supporting columns. Both columns are adjustable in height, they stand on wheels and are connected with a beam, which is running from one vertical beam to the other parallel to the floor. The gap of the supporting structure below gantry of the present invention is large enough to accommodate the beam. Imaging with Jackson tables with the patient inside the ring gantry requires a preparation step. The couch must be removed from the columns, and the ring gantry be positioned between the columns. This can be done in different ways: (a) by tilting the gantry on legs in a positive direction +100°, top behind, until it almost reaches the floor. One vertical column can now be lowered to its minimum position and inserted in the ring from below. After tilting the gantry back to a horizontal scan position, the couch can be mounted and patient prepared. The ring gantry is now ready for imaging. (b) It is also possible to step over the beam above floor laterally. For this purpose, the present invention comprises at least one linear actuator, a telescopic spindle drive vertical column, inside the supporting structure. The actuator can be put up to lift the supporting structure, gantry and one leg a few centimeters above floor. This leg can subsequently be rotated about its hip joint, to open space for the horizontal beam of the Jackson table. After insertion of the beam below the supporting structure, the leg can be lowered again and the actuator retracted. After insertion of the couch between vertical columns, the ring gantry is ready for imaging.

Cleaning of Wheels

In an OR, medical equipment must be clean and attention must also be paid to wheels which are potentially contaminated. Cleaning of wheels and servicing of drive units can be done with the present invention by putting up one linear actuator as described above to lift a leg, which can be rotated for cleaning or servicing. If two actuators are deployed, one to the right and one to the left inside the supporting structure, both legs and wheels therein can be cleaned and serviced.

Source

In one embodiment of the present invention, the X-ray source is an X-ray tube with rotating anode and a small anode angle, for example 10°, to provide a small effective focal spot size in nominal geometry with increased X-ray power output capacity due to enlarged focal spot length of line, i.e. width of focal spot track on the anode. The orientation of the tube and the rotating anode is essentially parallel to the symmetry axis of the ring gantry in order to avoid gyro momentums and mechanical stress to the rotating anode and bearings, which are a limiting factor if faster source rotations in accelerated scan protocols are to be applied. In order to provide a homogeneous radiation field over a larger detector area with increased X-ray output at given anode heat capacity, the tube is tilted by some small angle with respect to the ring axis, e.g. 10°, to overcome the anode's heel-effect. This intended deviation of use from the X-ray tube's nominal emission cone results in increased X-ray output and spectral stability in directions more perpendicular to the anode's surface and better homogeneity and slightly improved thermal stability at still acceptable gyro momentums for the cost of slightly increased effective focal spot isotropy and size (effective anode angle for effective focal spot size evaluations as per the example above increased to 20°). The source can be operated continuously (e.g. for fluoroscopic applications) or in pulsed mode.

Output Modulation

During a 3D scan with a specified X-ray energy, the shape and atomic composition of the object to be scanned determines its attenuation, which may vary from projection angle to projection angle. In order to minimize X-ray dose to the patient, it has been realized in prior art CT to adjust the X-ray output (i.e. the dose rate) per gantry angle electronically in a way that higher X-ray exposure rates are applied at angles of higher object attenuation, either by variation of the tube current [mA] or by variation of the pulse length [ms]. In one embodiment of the present invention, by means of the motion control system, the speed of rotation of the source (master) and all following axis, i.e. detector and collimator jaws (slave), may be adjusted accordingly to similarly adjust the number of X-ray photons emitted per source angle to scan the object with a constant X-ray emission rate at the source, such that the average dose rate and dynamic range of signal on the detector side can be kept rather constant during the rotation. For certain clinical applications, a higher imaging dose may be required for increased signal to noise ratio in reconstructed 3D volumes, typically implying that higher X-ray tube currents [mA] have to be used at high voltages [kV], therefore high X-ray power [W] is required. X-ray tubes with rotating anodes and small focal spot sizes are limited in dose output and power if the tube is cold, because of tungsten-rhenium alloys, commonly used as target material, being brittle at room temperatures and sensitive to the high temperature gradients in the focal spot achieved at higher X-ray powers, with mechanical tension and stress resulting in fissures and cracks at the anode's surface and damage of the tube. For this reason, warmup procedures are typically required and faster rotating tubes are deployed with prior art CT, being more sensitive to gyroscopic effects if tilted with respect to the gantry axis. In a surgical setting, warmup procedures are impractical because no warmup dose shall be applied to patient or staff. Therefore, the motion control system of the present invention is programmed to vary the speed of master source and trajectories of all slave axes according to the current heat load of the anode: At cold conditions, the X-ray power is limited but can be increased once the brittle-ductile temperature of the anode's target material is reached. So any (adaptive) FOV acquisition can start without warmup required at lower speed, accelerating the velocity of trajectories once the tube is getting warmer during the acquisition.

Primary Aperture

In order to reduce the amount of out-of-focus radiation (head scatter, OOF radiation), which is mainly due to Röntgen-Bremsstrahlungs photons emitted from areas on the anode lateral to the focal spot line, which are generated by backscattered and re-accelerated electrons impinging the anode, a primary aperture has been designed to be used in one embodiment of the present invention and to be inserted in closest proximity to the focal spot at the X-ray tubes' exit window. The primary aperture is shaped such that it attenuates most of the primary radiation in emission angles not required for the specific, flexible geometry: It collimates the primary beam strongly in the longitudinal direction (for example <20°), and keeps the lateral emission angle very wide (for example >60°) to accommodate non-isocentric image acquisitions with larger offset angles between source and opposing detector for ultra-large field of view (FOV) acquisitions. The lateral collimation may be designed asymmetrically (for example to 40°) to be more effective in shielding of lateral OOF radiation, if detector offset angles are constrained to only positive (or only negative) angles relative to source.

Flattening Filter

In one embodiment of the present invention, a flattening filter, made of machined aluminum of varying thickness in a direction essentially longitudinally to the ring and the rotating anode's axis can be inserted in the X-ray cone to compensate for the self-attenuation inside the target material of the anode (Heel effect). The flattening filter would generate a more homogeneous X-ray output in the longitudinal direction but not reduce the dose output in the direction of rays of already reduced output due to the Heel effect. The flattening filter can be used to increase the inherent filtration of X-ray tubes at the relevant central axis according to the system's geometry, whereby a minimum aluminum equivalent filtration may be required legally depending on country-specific laws and medical application. The flattening filter may be deployed in a fixed position with the source and primary aperture and may help to reduce the amount of scatter generated in the object by reducing the peak of unfiltered X-ray emission in the central field and thus the amount of scatter to the level at the field border.

Collimator

The present invention describes a collimator comprising four independently moving jaws, a movable filter carriage with optional field light, a rotatable filter wheel and line lasers. All movable components are motorized and motion of components is controlled by a computerized motion control system, which cares for synchronicity of motion of source and X-ray emission.

Filter Carriage

In one embodiment of the present invention the source arm may be equipped with a motorized filter carriage to insert a bow tie filter as known from prior art into the primary beam, in order to reduce the primary radiation to areas where the object to be scanned has less attenuation, e.g. at the skin. The present invention allows to attach a customized beam modulating insert to the filter carriage and to move the 3D shape of this attenuator during source rotation to accommodate any variations in shape of patient. This reduces the dose to the patient and the amount of scatter being generated, thus may help to improve image quality. Since the present invention supports adaptive FOV acquisitions, the bow tie shape of the attenuator would have to be adapted to each individual clinical situation. This can be achieved to some extent with the present invention by using the filter carriage not in a binary way (in out) but to position a three dimensionally shaped attenuator such that a variety of different fluence distributions can be generated. In a simple implementation, the carriage can hold a set of bow tie filters, optimized for different, predefined FOVs and scan protocols. In the present invention, the carriage is also prepared to insert a primary modulation grid with a high frequency pattern into the beam for the purpose of deriving and subtracting object scatter components in the projection images captured from the detector. Further, the multi-function carriage can be used to position a light-emitting diode (LED) with optics into the central axis of the X-ray beam to be used as a field size indicator for manual field size adjustments before X-ray exposure ("light field").

Filter Wheel

The present invention incorporates a filter wheel with a multiple of sectors which can be rotated around the filter wheel axis, whereby each sector holds a selectable filter material which can be rotated into the primary X-ray cone. Filter materials may be optimized for specific purposes in static filter wheel positions, e.g. a filter insert can be air (for use in combination with low energy X-rays) or copper (to attenuate low energy photons and create harder beams, to reduce skin dose and for pediatric imaging) or aluminum (to enlarge the inherent filtration of the X-ray tube). For dual energy applications, when short, low energy X-ray pulses (e.g. 80 kVp) are emitted alternatingly with short, high energy X-ray pulses (e.g. 150 kVp) at high frequencies (e.g. 10 Hz) for subsequent subtraction of projection images to allow for tissue characterization and separation of soft tissue from bony anatomy, it is helpful to separate the overlapping Röntgen-Bremsstrahlungs spectrae of low and high energy pulses as good as possible. For this purpose, in one embodiment, the present invention makes use of a filter wheel insert consisting of silver (to attenuate low energy photons) and copper (to attenuate the characteristic Bremsstrahlungs peaks of silver). The filter wheel is then spinning with a frequency of half the pulse repetition frequency of the X-ray source in order to provide the air-insert for the low energy pulse and the 180° opposite beam hardening insert for the high energy pulse as they are emitted, respectively. In another embodiment of the present invention, the filter wheel may be divided symmetrically in two opposing sectors, which can be equipped with concentrically aligned, attenuating ring sectors, each of the both sectors consisting of multiple blocker ring sectors radially separated by ring sectors of air, whereby the two opposing sectors alternate blocker and air in radial direction of the filter wheel, such that if the filter wheel spins in pulsed X-ray mode it will block an essentially 50% portion of the primary X-ray beam in one pulse and the other 50% portion of the primary X-ray beam in the next pulse. By such, the present invention provides a mechanical solution for a binary stopping array (BSA) if the X-ray source is operated in pulsed mode, whereby a pixel on the detector behind the blocker measures object scatter only and same pixel will be exposed to primary plus scatter radiation in the next frame. In each image, the scatter can be interpolated and subtracted, e.g. during backprojection.

Line Lasers on Source

In one embodiment of the present invention, a pair of line lasers are deployed with the collimator to project a cross hair onto the skin of the patient which can be used to define the imaging center manually. For this purpose, a first line laser can be statically mounted to project the plan of rotation (circular trajectory) onto the patient. Because of independent rotation of source and detector and because of the collimator's possibility to dynamically collimate the X-ray beam in non-isocentric directions, the second line laser must be adjustable to point in the direction of the middle of the field (between x1 and x2 jaws). For this purpose, similar zo movable line lasers on the detector described below, a second line laser is installed on a carriage on rails moving essentially in a direction parallel to the motion of x-jaws, whereby the laser line can be adjusted to pivot about an axis perpendicular to rails, essentially simulating a laser beam being emitted from the focal spot of the source and directed to the center of the currently adjusted field. By such means, the laser cross hair projection can be used to adjust the 3D imaging center and thus to generate the respective non-isocentric trajectories for subsequent acquisitions.

Fluence Modulation

By means of the built-in collimator, the present invention can be turned from a CBCT system to a CT system, effectively collimating the primary X-ray cone beam to a fan beam, thus reducing the amount of object scatter significantly. Collimation can be used more generically in longitudinal and lateral direction to expose only such volumes of the object where information is required from rays passing through the object in certain directions. By limiting the X-ray field size in all directions, the dose to patient and the amount of scatter being generated in the object can be reduced. In radiation therapy, it is required to provide volumetric scans with accurate attenuation values or CT Hounsfield units [HU], sufficient for treatment planning, accurate dose calculation and adaptive treatment. CT units with fan beam geometry and anti-scatter collimation at the detector provide gold standard data for accurate treatment planning, and prior art CBCT is widely considered to be inaccurate because of scattered dose and non-reliable HU calibration, which is dependent on the field size, size of object and atomic composition of the object. However, a narrow CT's fan beam is less efficient in terms of X-ray usage, because most of the generated photons are bumped into the collimation. This results in higher heat capacity requirements for the X-ray tube and deployment of effectively larger tubes in prior art CTs. Due to the short scan length of a narrow fan beam, multiple rotations have to be performed in helical scans to cover a longitudinally extended FOV, typically requiring a motorized patient couch. To reduce the scan times to clinically acceptable values, a high speed of rotation is required and X-ray power and detector signals have to be transmitted via slip rings, which are technically complex, heavy and expensive compared to conventional wiring. These are all limiting factors for flexible mobility of low-cost imaging systems and constrain wider usage of image guided procedures in medical interventions for the sake of patients.

The present invention uses the built-in collimator to dynamically change the field aperture also in the longitudinal direction. The object scatter contribution of an open field CBCT projection can be directly measured by comparing it with a fan beam projection. By subtraction of the image scatter component from the cone beam projection, an essentially scatter-free planar image can be derived and used for accurate reconstruction of HU values. For this purpose, a slit beam can be collimated and moved longitudinally over the extent of the FOV, so that for each pixel on the detector the scatter subtraction can be performed. Because of the distribution of scatter on the detector plane, which is effectively a blurry image with dominant low frequency components and which is not changing too much from projection to projection if the detector frame rate is high enough and which can be estimated by extrapolation and interpolation techniques in longitudinal direction if captured in a single slice at the central axis and behind the jaws at superior and inferior border of the ROI, this technique may be implemented in one embodiment of the present invention in such a way that a limited number of slit beam projections are acquired from different source angles in the central axis of the imaging system in one first rotation (CT scan), while a subsequent second rotation may capture the adaptive field CBCT projections, which can be scatter corrected inline, during the acquisition, causing no further system latencies. In order to save time for the first rotation, a modulation of the longitudinal field length during one rotation by means of the collimator's y-jaws would also yield information about the object scatter: For a stationary geometry, the measured pixel intensity at the detector, which is the sum of primary radiation and object scatter, decreases continuously when the field length shrinks from a larger extent to a narrower beam and it reaches a minimum value, the attenuated primary radiation, at zero field size (fan beam). This connection between field size and scatter can be plotted in a graph. It is possible to estimate the amount of scatter and therefore derive the primary by extrapolation of the graph towards the zero filed size. In one embodiment of the present invention, during adaptive FOV CBCT acquisition, the dynamic collimation of the X-ray field may be modified in a way that jaws are oscillating during the exposure and rotation to modulate the amount of scatter generated in order to estimate the total scatter and subtract it in the projection domain.

Detector Perturbation

Due to independently moving rings of source and detector and dynamic collimation, the present invention provides the possibility of changing the offset between source and detector during exposures. This may be of help even in simple isocentric SFOV acquisitions, where normally the detector is just opposite to the source in prior art CBCT. Under such conditions, central pixels on the detector would back-project on concentric circles in the 3D volume. On real-world detectors, the pixel response to dose is not perfect and may vary from pixel to pixel by small intensity values. This imperfection produces circular artifacts around the imaging center in the reconstruction of prior art CBCT. By introducing a detector perturbation in the acquisition trajectories, such that the detector oscillates a little during the rotation in the direction of rotation, effectively accelerating to rotate faster than the source and decelerating to slow down and let the source catch up again, the pixel statistics in the back-projection can be significantly improved. For this purpose, the perturbation offset needs to vary from one image frame to the next ideally corresponds to the angle one pixel stretches to the imaging center, such that a lower responding detector pixel would not be back-projected at a circle but into a broader area in the 3D volume. Circular ring artifacts can be eliminated by this technique without losing spatial resolution.

Anti-Scatter Grid

In one embodiment of the present invention, the detector can be a flat panel detector, for example either an amorphous silicon flat panel with a scintillating layer or a CMOS detector or a spectral detector, which allows to discriminate energies of incident photons, suitable for X-ray imaging. To remove scattered radiation from the entrance window of the detector, an anti-scatter grid may be deployed. In prior art X-ray technology, mainly focused grids are in use which would remove scattered radiation from sources not coinciding with the focus of the X-ray source for the cost of some absorption of primary radiation inside the grid and with all kinds of artifacts, if the grid is not perfectly aligned with the source or if the grid spacing is in the same order of magnitude as the detector's pixel pitch (inhomogeneous detector response, grid cut-off, Moiré patterns, line artifacts. It is recommended in radiology, not to use anti-scatter grids for pediatric imaging because of the higher exposures and dose to the patient required. In one embodiment of the present invention, a movable scatter grid is mounted on the surface of the flat panel detector. The line grid is as wide as the detector, but may be shorter in the longitudinal direction to be retracted in a storage area essentially behind the active area of the panel in case it is not used during an acquisition. For CBCT or fan beam acquisition, it may be inserted into the primary beam by means of a motorized carriage, moving the grid along rails in longitudinal direction, supporting it at both sides of the panel. Because of the flexible geometry of the present invention with variable angle between source and detector, only a one-dimensional anti-scatter grid (line grid) can be applied, with the lines orthogonal to the ring axis. During exposures in high resolution imaging with the parallel line grid deployed, the grid's longitudinal position can be varied slightly by means of the motors, such that the grid moves continuously at a constant speed or oscillates in the longitudinal direction in order to blur the effects of interference of projected grid lines with the detector's pixel grid.

12 DOF Geometric Correction

Gravitational force leads to position-dependent displacements of all moving components. A sole translational correction of this "flex" is usually not sufficient to determine the exact geometry for every independent position of the rotating arms. In the embodiment of the present invention, we incorporated a 12 degrees of freedom (DOF) flex correction that comprises gantry-angle dependent offsets in three translations and three rotations of the X-ray source as well as three translations and three rotations of the detector. The three rotational components of the X-ray source and collimation can be determined by analyzing the jaw penumbras of dynamically collimated X-ray beams on the flat-panel detector. For this purpose, a cylindrical phantom with an arrangement of multiple steel balls can be attached to the supporting structure. During a scan, the radio-opaque marker balls with known coordinates in 3D space are projected onto the detector plane. From the coordinates of marker balls in the 2D plane, the 12 DOF can be determined and used for subsequent correction of the imaging metrics for increased spatial resolution and accuracy of scans.

Panoramic Planar Imaging

In one embodiment of the present invention, the system is used to acquire X-ray images at different detector positions while keeping the X-ray source at the same position to create panoramic planar images achieving lateral field sizes that are much larger than what a single detector position can cover. The set of X-ray images are projected onto a common perpendicular plane and then stitched to a single panoramic image.

MeV Imaging

The motorized carriage described above can also be used to move a build-up layer over the active area of the detector, for example a sheet of copper with 1.5 mm thickness, to enhance the detector's response for radiation of higher energies, e.g. photons in the MeV range. Due to the degree of freedom for independent rotation of arms, such MeV imaging capabilities may be of use in combination of the present invention with external sources of radiation, such as linear accelerators in radiation therapy or particle sources, for example protons or carbon ions. With appropriate build-ups and proper selection of radiation-hard panel types, the same detector can be used for photons in the keV range as well as photons/protons in the MeV range.

Moveable Lasers on Detector Arm

In medical imaging systems of prior art, line lasers are deployed at gantry or source to mark the fixed imaging center with a cross hair projection, e.g. the center of a CT bore and the imaging plane. In the present invention, the imaging center is variable and can be set anywhere inside the ring gantry. In a surgical setting, when the sterile detector is placed above the patient and the potentially contaminated source is located below patient and couch, laser lines can be projected onto the skin of the patient from the detector arm. In one embodiment of the present invention, four independently moving line lasers are attached to carriages on rails in the detector arm, moving next to the detector, alongside to the four sides of the active area. Each of the four line lasers projects a laser line perpendicular to direction of motion along the rails. Each of the four laser lines can pivot on the carriage in order to always direct the laser to the X-ray source focal spot. This is for example feasible if the detector is not exactly opposite to the source. If only two of the four line lasers are turned on, they can be used to project a cross hair onto the skin of the patient, marking for example the X-ray beam's central axis or for example another point of interest. These cross hair line projections can be used to visually adjust the imaging center inside the ring gantry at the ROI by rotating the detector and the source. If all four lasers are turned on, the projected lines can be used to visualize and adjust the field-size of a planar X-ray exposure. The field-size of the planar X-ray exposure is also called field of view or FOV. For this application, the positions of four laser carriages on rails and inclination of line lasers corresponds with the four collimator jaw positions, effectively projecting the exit of the X-ray beam after traversing the patient inversely onto the patient's skin. In a technical implementation of the described laser system, small optical line lasers are rigidly attached to the carriage, emitting a laser line into an optical prism, which is rotated by a small stepper motor on the carriage to mirror the laser line in the direction towards the X-ray focal spot, which position is always known by the system's motion control system. Detector, carriages and rails are covered by a transparent plastic cover, e.g. a polycarbonate window.

Passive Tracking

For usage of the present invention in image guided maneuvers in combination with external systems, such as beam delivery systems in radiation therapy or robotic manipulators in surgery which are operating in a room coordinate system defined by a room isocenter, it may be required to track the gantry by means of an external tracking system in order to determine its position and orientation relative to the room coordinate system. For this purpose, active or passive markers may be attached to the inner, front or backside of the gantry; markers may also be attached to the outer stationary ring for improved visibility by tracking cameras.

Computer Vision—Active Tracking

In one embodiment of the present invention, the detector arm is equipped with stereoscopic cameras, which can be used to capture images or record videos of the medical intervention or to monitor the patient remotely from any side, for example in radiation therapy. More advanced use-cases for the stereoscopic cameras comprise the ability to acquire 3D surface scans of the whole circumference of the patient by rotating the detector arm to accomplish the desired scan without shadow artifacts. 3D surface scans may also be acquired in real time during medical interventions, to capture motion of patient, e.g. breathing, for gating applications or for phase binning in 4D CT or CBCT scans. For this purpose, a video projector may also be mounted on the detector arm. In addition to the detector mounted line lasers described above, the video projector may serve to project structure light, e.g. random patterns or grey code stripe sequences, onto the skin of the patient for accurate surface scanning applications. The projector can also be used to back-project patient-specific information onto the skin of the patient, once the surface is captured, in order to assist the medical team by augmented reality (AR). As an example, the shape and location of organs, vertebrae (along with their identification) and current vital parameters can be projected. Furthermore, the cameras mounted on the detector arm may be used to track surgical instruments or markers on tools. The advantage of having integrated tracking cameras on the detector arm and in the ring gantry in comparison to external tracking systems is that the internal cameras can be factory calibrated in the frame of the rigid gantry, identical to the X-ray source and detector, which provide accurately reconstructed X-ray volumes in the gantry's imaging coordinate system. Therefore, no additional cross-calibration or co-registration of external tracking system data to patient volume dataset is required with the patient in situ, which may help to increase efficacy and overall accuracy of image guided medical interventions. As an example, surgical instruments with optical markers may be captured and, for example, the tip of a biopsy needle in situ may be visualized in the 3D CBCT volume or in a pair of orthogonal planar X-ray projections at a certain point in time (time of X-ray acquisition), while the actual position of the needle can be superimposed precisely based on the information from the internal tracking cameras in real time, without additionally required user interaction (calibration, co-registration of optical system and X-ray system).

In another embodiment of the present invention, the source arm (as well as arms on other rotating rings) are equipped with optical cameras to track patient or instruments.

In another embodiment of the present invention, the ring gantry itself is equipped with stereoscopic cameras to track patient and instruments independent of the detector or source rotation. The rigid ring gantry design as described above offers space for such cameras and video projectors, which can easily be wired through the stationary inner ring of the gantry.

In another embodiment of the present invention, the supporting structure and legs are also equipped with cameras to provide video information during motion of system, capturing the floor (e.g. during helical scans) and room with walls, OR table, obstacles in path the surrounding scene. For example, leg mounted cameras can be LIDAR scanners to support autonomous motion.

In another embodiment of the present invention, the hand held HMI is equipped with cameras to film the imaging system and patient/scene from a distant position. The position and orientation of the movable components of the imaging system or the position and orientation of the complete mobile system with respect to patient/scene and operator (holding the camera) can be determined from these images in real time. By such, the observer's viewing point with respect to the system is known, and joy stick functionality to control motion of system in a certain direction can be adapted accordingly, i.e. rotate the system clockwise in positive direction if viewed from behind and rotate in negative direction if viewed from in front of the gantry. This functionality can also be established by means of gyroscopic sensors integrated into the HMI determining the relative orientation with respect to the system (can be nulled on docking point of HMI on gantry).

All optical cameras on board can also be used to determine position and orientation of the mobile system within a room coordinate system, by co-registration of room based marker fiducials or other room based features. For example, during helical scans, the longitudinal position of the system is an important input to the reconstruction pipeline for every projection frame. The wheel drive system may not be as accurate as required at rough or uneven surfaces of floor, but tracking the texture of the floor during motion can provide accurate information of position of system during scans. This information can be combined with inclinometer readout values from inclinometers mounted on gantry or supporting structure. The cameras on board can also be used for collision avoidance purposes during a scan or free motion. In one embodiment of the present invention the system is supported by four laser distance sensors, two at the source arm and two at the detector arm, pointing in an essentially longitudinal direction alongside of both sides of the arm, away from the gantry, such that the laser distance sensors can stop any rotation of arms and stop any gantry tilt or wheel forward motion if an obstacle (patient, staff, OR table etc.) is detected. Cameras and laser distance sensors are designed to support autonomous motion of the whole robotic system in a hospital environment.

Further Rings

In another embodiment of the present invention, in addition to independently rotating arms of X-ray source and detector, further rotating and motorized rings may be deployed with the ring gantry if arranged next to the stationary outer ring. One additional rotating ring may position a robotic arm to assist the medical team during interventions. For example, the robotic arm may serve as a holder for instruments, sonographic sensors, surface scanners or video projectors. The robotic arm may be rotated in any useful position around the patient. Identical to X-ray system and optical scanners, the robotic arm moves in a pre-calibrated coordinate system of the rigid ring gantry, and can therefore be programmed to perform any manipulation at highest possible precision without a need for additional cross-system calibrations. Two further rings on the gantry might support two robotic arms for image guided, robotic surgery.

In the following, the invention will be described in more detail with reference to the Figures.

FIG. 1 shows a preferred embodiment of the present invention, providing a mobile imaging system for use in medical interventions, in particular for use in radiotherapy or surgery. FIG. 1 schematically illustrates the mobile imaging ring system according to an embodiment of the present invention. The system comprises gantry 1, a detachable human machine interface (HMI) 2, such as a tablet with touch screen, joysticks, button controls, dead man switches and e-stop. The docking point of the HMI on the gantry allows to rotate the HMI relative to gantry into a convenient position for the user, even when the gantry is tilted. The system further comprises an e-stop button 3, a left leg 4 on wheels with a hip joint, a supporting structure 5 including power supplies, drive controls, PLC, X-ray power and signal processing, X-ray arm 6 including a source and a collimator), detector arm 7 with a panel and cameras and a right leg 8 on wheels.

FIG. 2 illustrates the independent motion of rings, exemplarily showing three positions of the detector arm 1 and the source arm 2. The left figure shows the parking position with source situated at the bottom of the system and the detector above the source. The figure in the middle shows a non-isocentric imaging position wherein the X-ray beam is collimated to the active area of detector, whereas the right figure show the lateral imaging, i.e. isocentric position.

FIG. 3 illustrates non-isocentric small circular field of view (SFOV) acquisition. In clinical situations, the region of interest ROI, i.e. the object to be examined, can be off-centered from the ring center. Source and detector virtually rotate around an imaging center, that is a point inside the ROI, with varying speed of rotation along the circular ring, such that equidistant angles per time interval are traveled, resulting in uniform distribution of scanning photons and frames from the object's perspective.

FIG. 4 illustrates the use of two separate detector to X-ray source offsets, as illustrated in the left figure, allowing the acquisition and patching (also referred to as stitching) of two X-ray images to a single panoramic image projected onto a perpendicular plane for recording panoramic planar images.

In FIG. 5, the top figure illustrates the geometry used in adaptive large FOV acquisitions. A 3D mesh of object (e.g. from preinterventional DICOM data or intra-interventional surface scan) is used for adaptive FOV trajectory generation, including dynamic collimation to the intended target. The middle figure shows a resulting limited ROI scan (prostate) and a large FOV scan (pelvis) in transaxial and coronal slices. Dotted lines represent the predefined convex hull of the FOV. Note that image information is also available outside the FOV, with anisotroic modulation transfer function (MTF)—tomosynthesis. In the bottom figure, ultra-low dose limited ROI acquisition (vertebrae) is shown.

FIG. 6 illustrates the geometry used in isocentric short-scan CBCT trajectory with collimation jaw fade-out towards the end of the trajectory to physically avoid redundant information and spare dose to patient, e.g. in head scans, when the lenses of the patient need to be spared, attenuated X-ray exit dose only. It is noted that the geometry shown in FIG. 6 works also for non-isocentric imaging.

FIG. 7 exemplary shows an isocentric dual short-scan CBCT trajectory. The left figure shows the clockwise first short-scan (x-ray on), and the right figure shows the source-detector offset change (x-ray off) and counter-clockwise second short-scan (x-ray on). Again, the geometry equally works for non-isocentric imaging.

Figure 1:
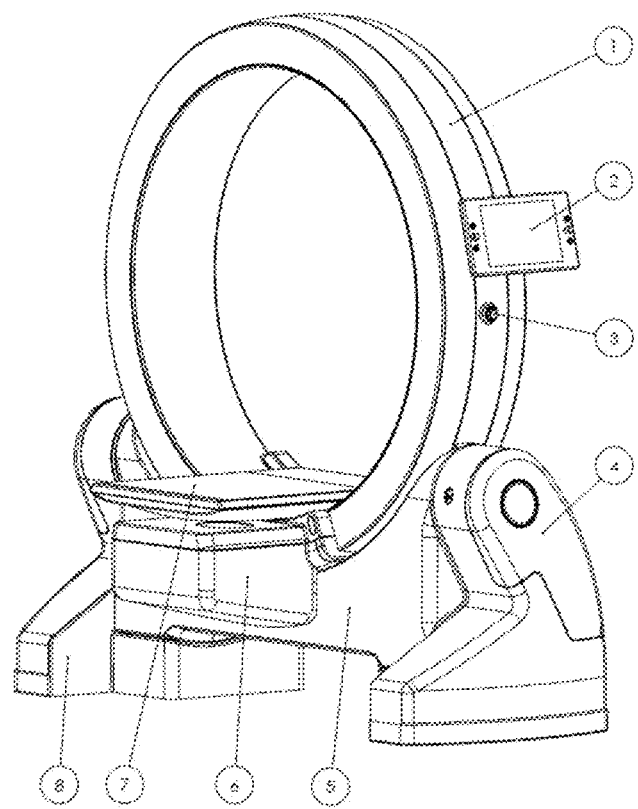
Figure 2:
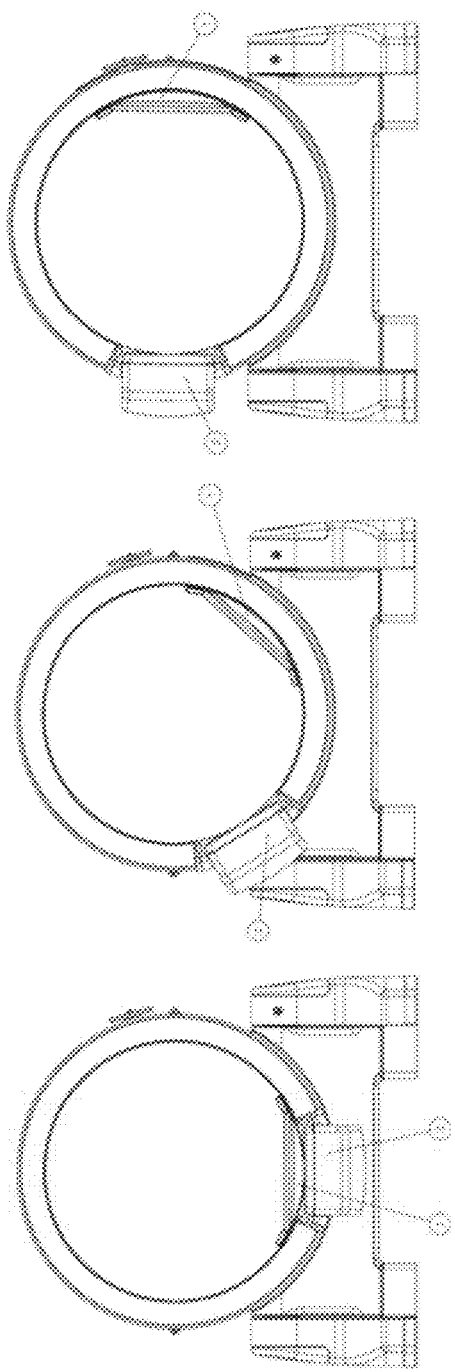
Figure 3:
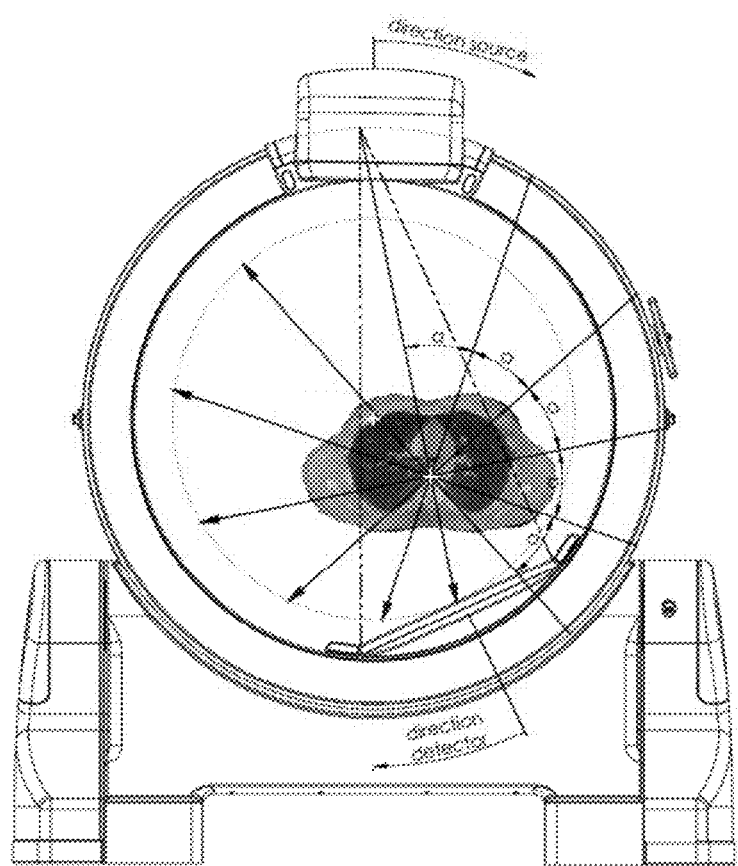
Figure 4:
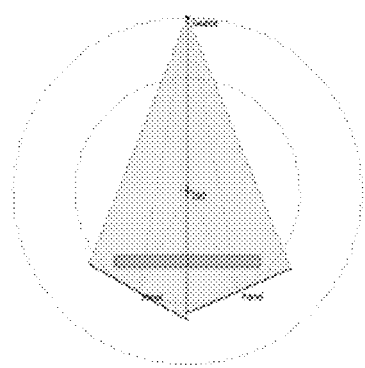
Figure 4:
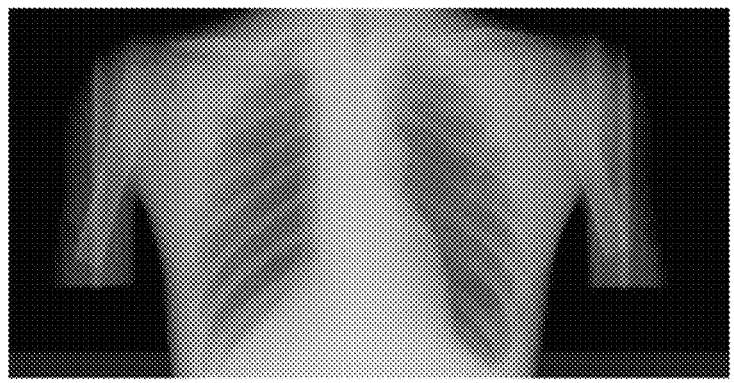
Figure 5:
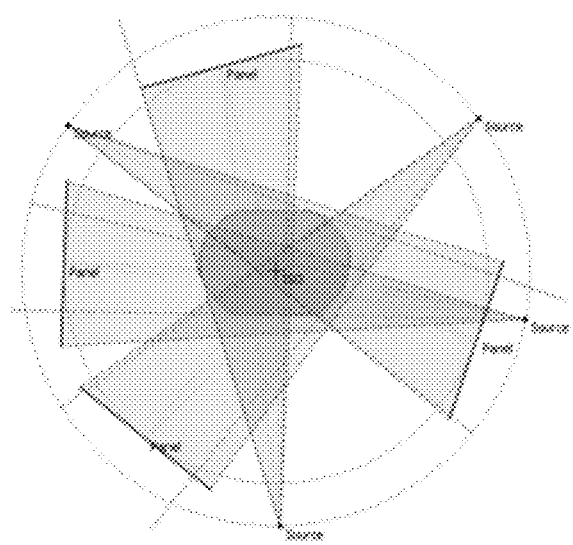
Figure 5:
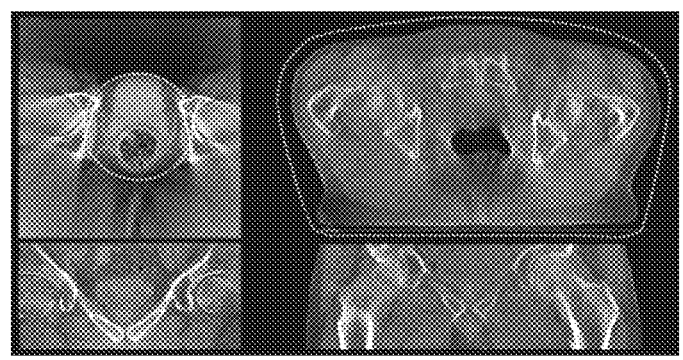
Figure 5:
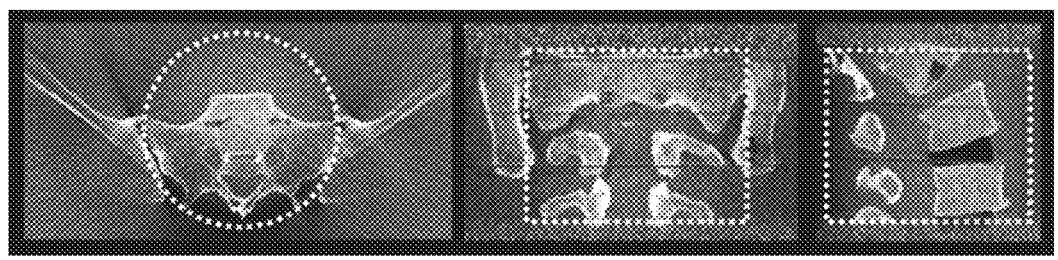
Figure 6:
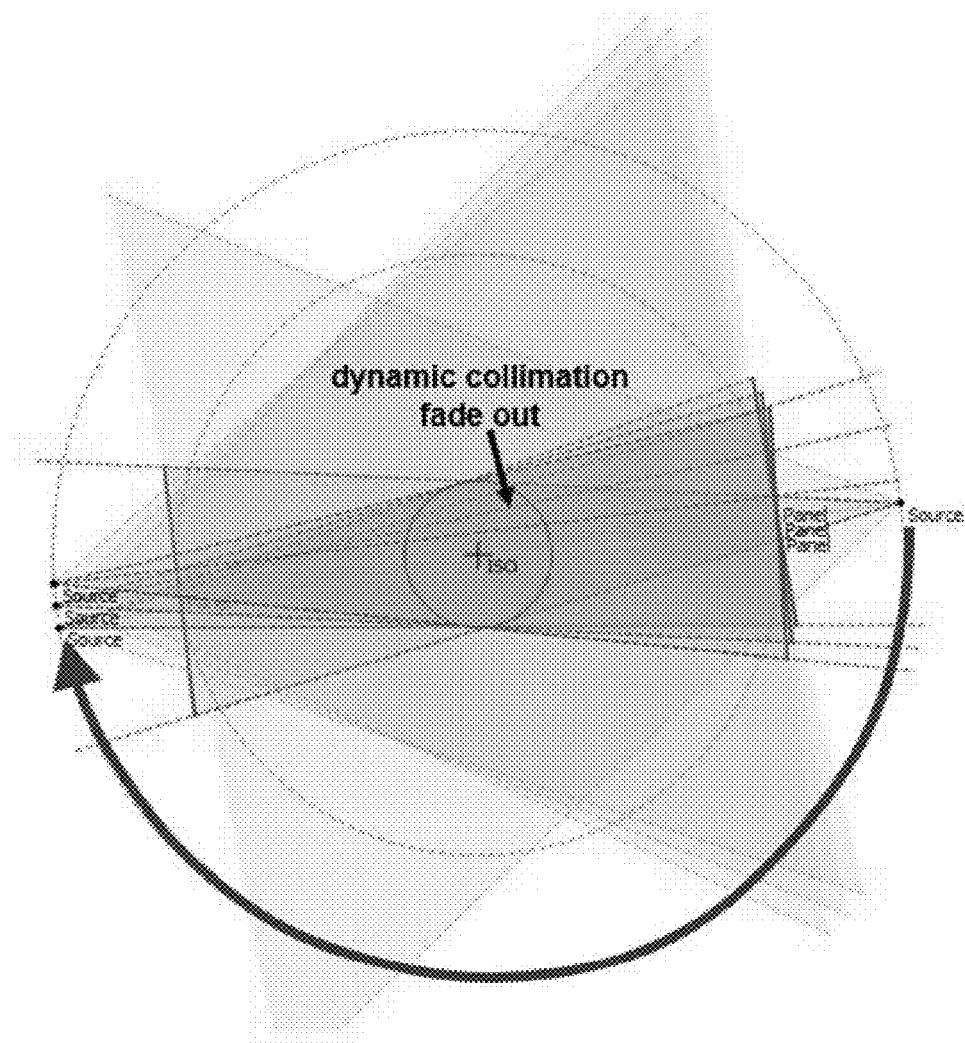
Figure 7:
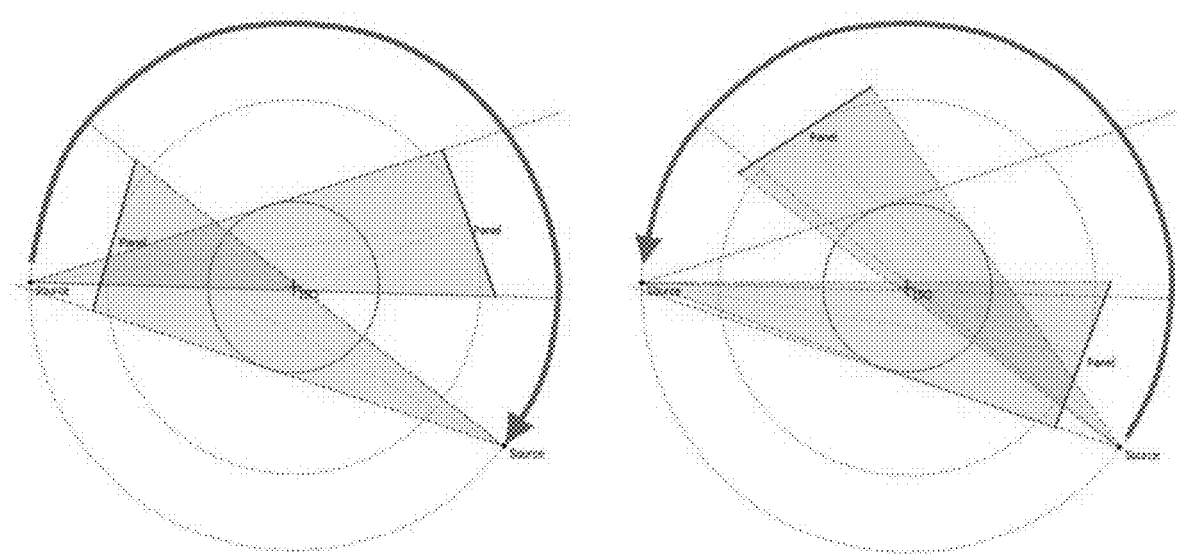
Figure 8:
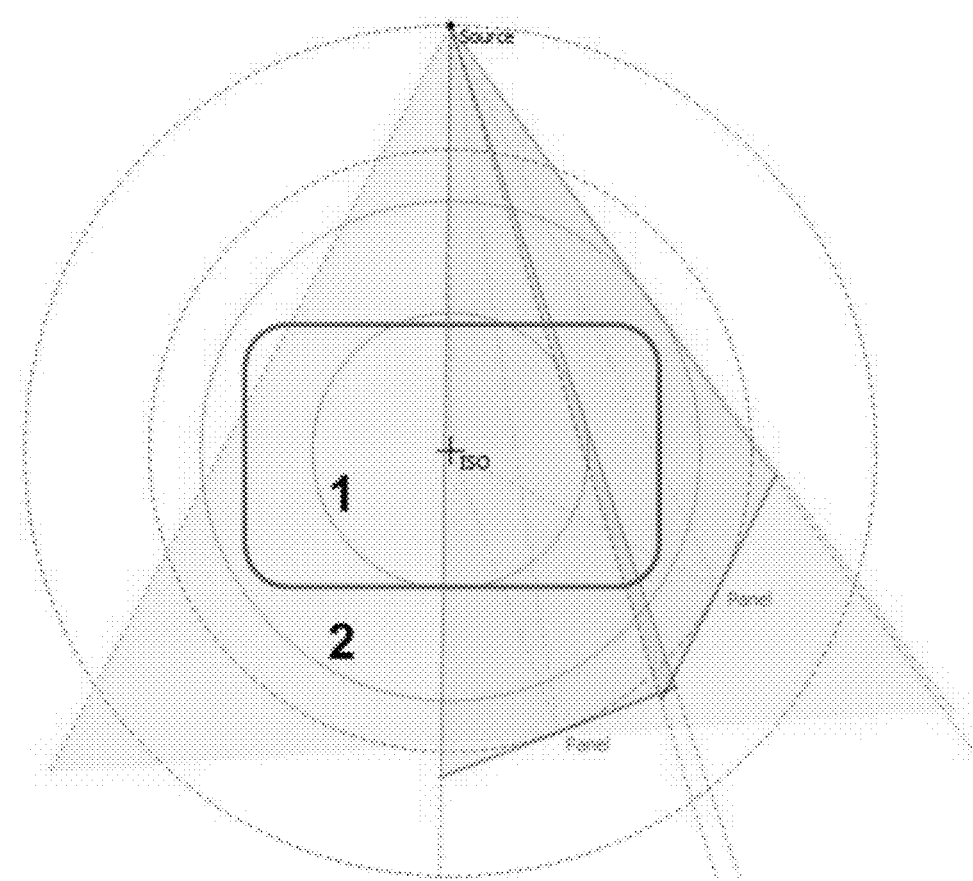
FIG. 8 shows the schematic trajectory of the ultra large field of view (LFOV) that combines a regular LFOV imaging trajectory (inner circle 1) and a second ring trajectory that covers only the outer parts of the radial FOV ("donut"—outer circle 2).
Figure 9:
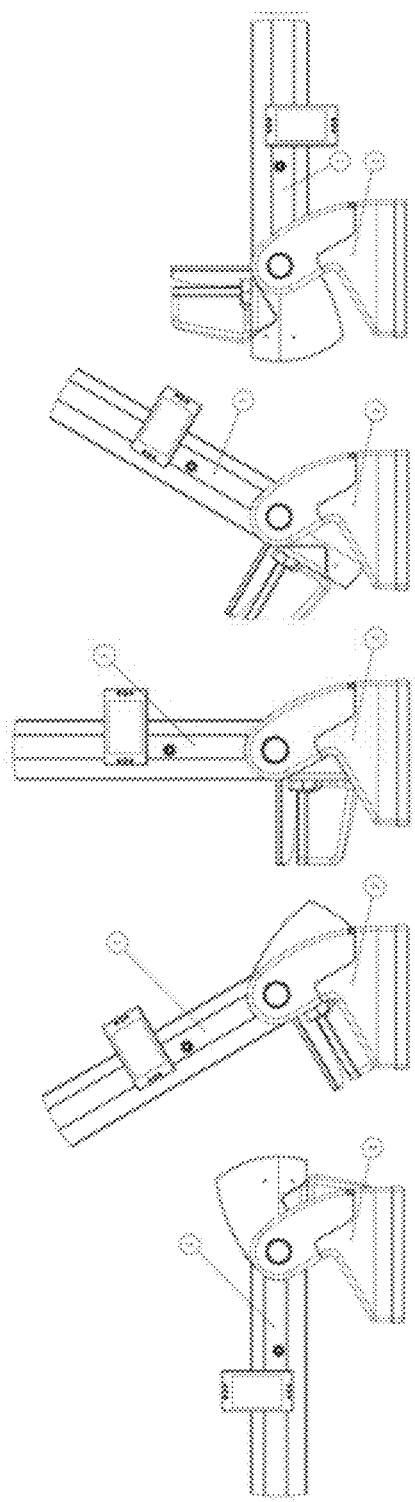
FIG. 9 illustrates the possibility of tilting the gantry, showing the stationary outer ring 1 of the ring gantry and leg 2 with hip joint.
Figure 10:
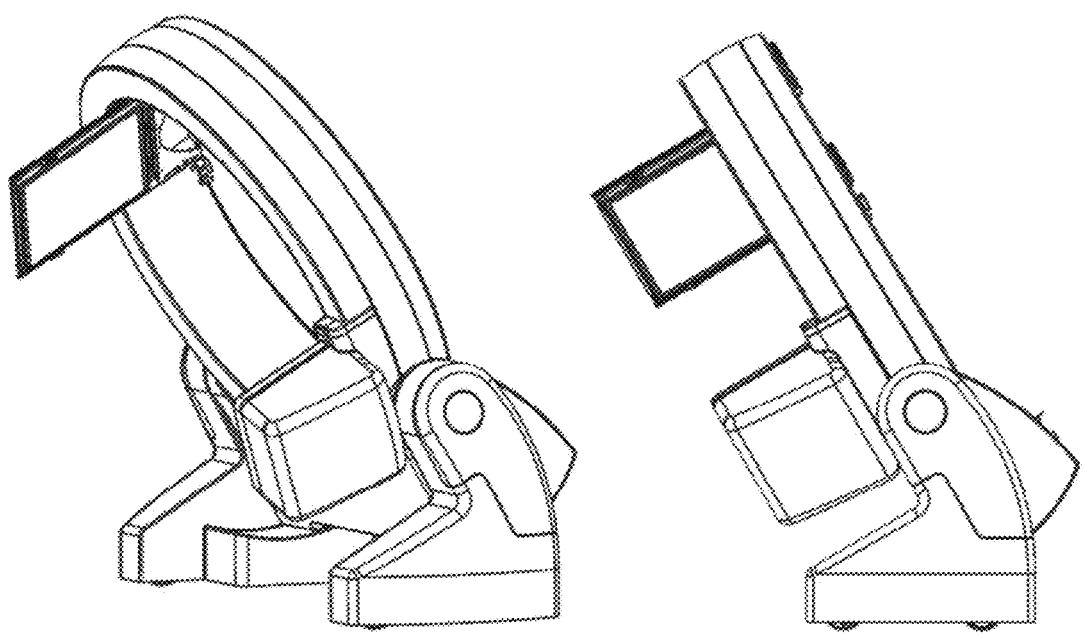

In FIG. 10, illustrates the specific structure of the system according of the present invention, allowing the source to freely rotate 360° even if gantry is tilted.

Figure 11:
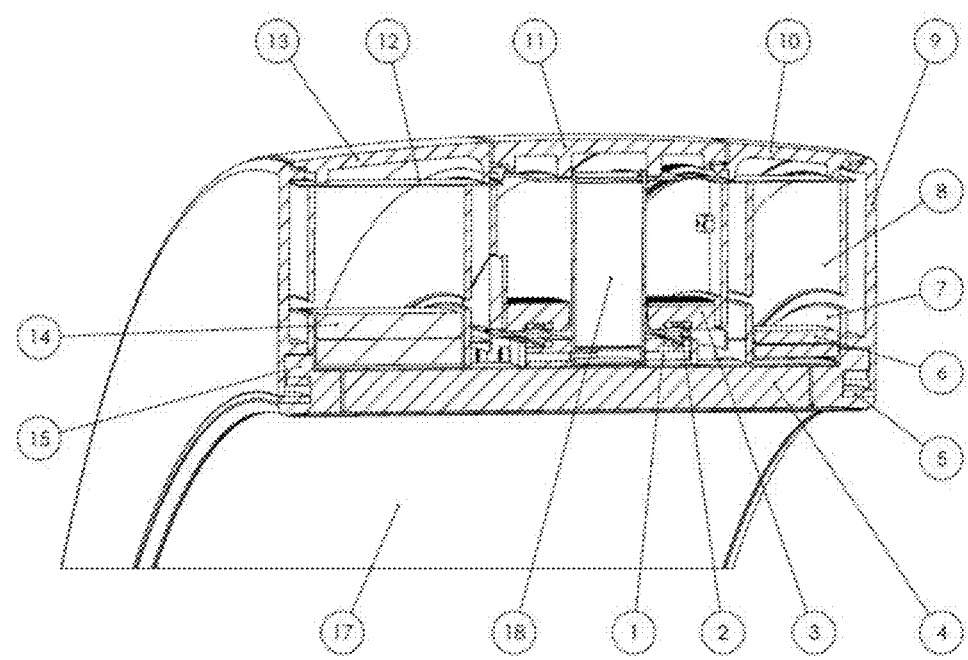

FIG. 11 shows a schematic cross section of the gantry. The gantry includes an inner bearing ring 1 with screws to adjust the play of bearing, a large diameter high precision ball bearing 2, an outer gear wheel 3 for a toothed belt, an inner stationary ring 4 made, e.g. of aluminum honeycomb compound for providing space for tracking cameras and video projectors directed to the imaging center of the gantry, a transparent plastic 5 provided as diffusor for ring LED illumination, flat cables 6 to the detector ring, a separator rings 7 and 8 to space fore rope loop retraction, the backside 9 of the ring, a rotating outer detector ring cover 10, a stationary outer ring 11, a rotating outer ring 12 providing for cable guidance, a rotating outer source ring cover 13, flat cables 14 to the source and the collimator, a bayonet locker 15 for the front ring, a stationary inner ring (bore) 17, and a stationary, rigid ring structure 18, preferably made of an aluminum honeycomb compound with cable insert and mechanical interface to supporting structure below the gantry.

Figure 12:
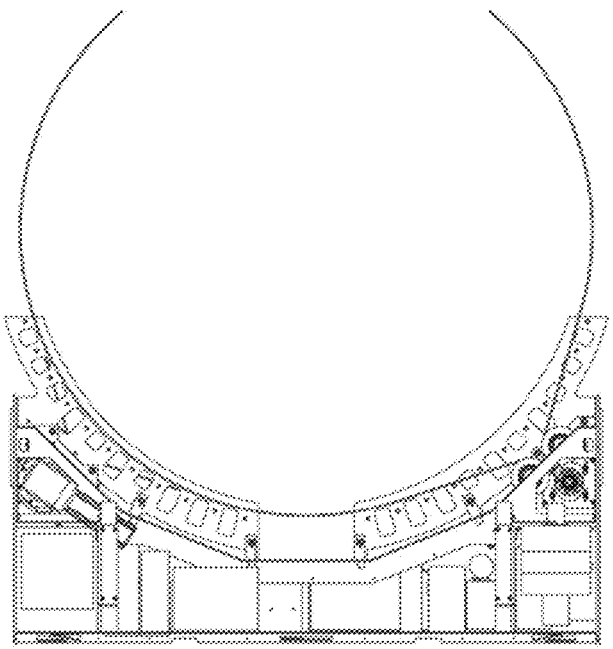
Figure 12:
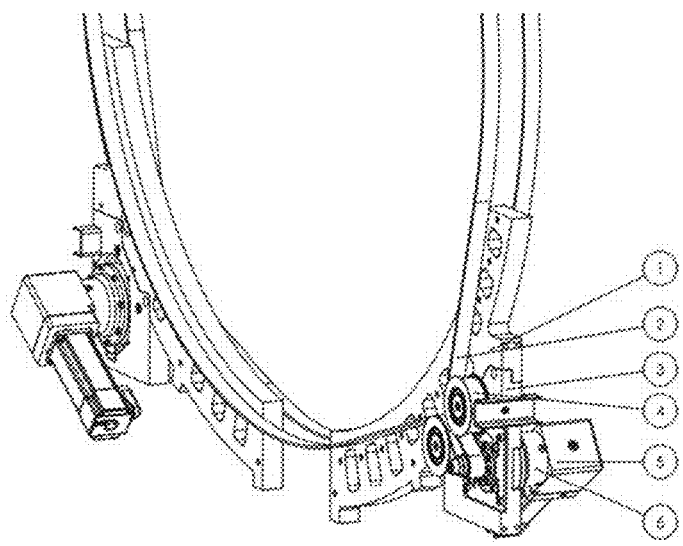

FIG. 12 shows a generic interface to the supporting structure and ring drives. In the upper figure, the mechanical interface to the gantry is shown, that incorporates drive units, power supplies, motor controllers, X-ray inverter, PLC, and a computer with GPU power for image processing and reconstruction. Cables are inserted into the gantry from below between the belts. In the lower figure insert 1, providing a mechanical interface between the gantry and the supporting structure, allowing the gantry to be reusable for any alternative mobility concept, a toothed belt 2, a preferably tensioned and clamped drive carriage 3, guide rollers 4, a 90° angle gear box 5, and a planetary gear 6. Additional rings can be coupled in the same way. Cables are inserted between belts at gap on bottom.

Figure 13:
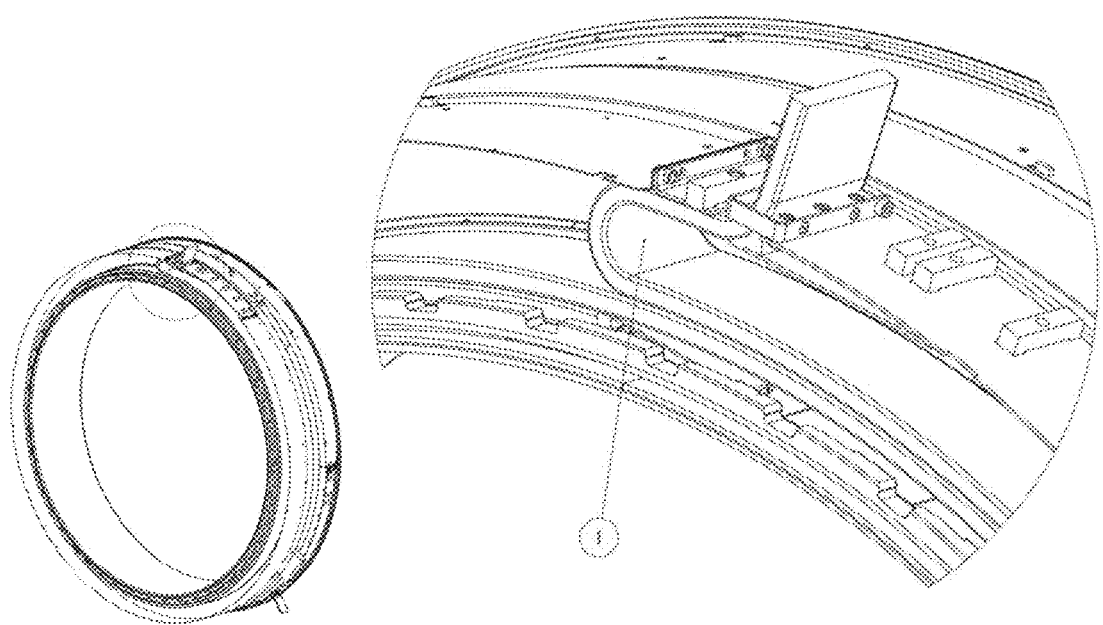

FIG. 13 illustrates a possibility of providing cable guidance wherein flat cables inside ring are clamped at insertion of the stationary inner ring and extraction of the rotating arm. The cable loop moves with half velocity of outer ring.

Figure 14:
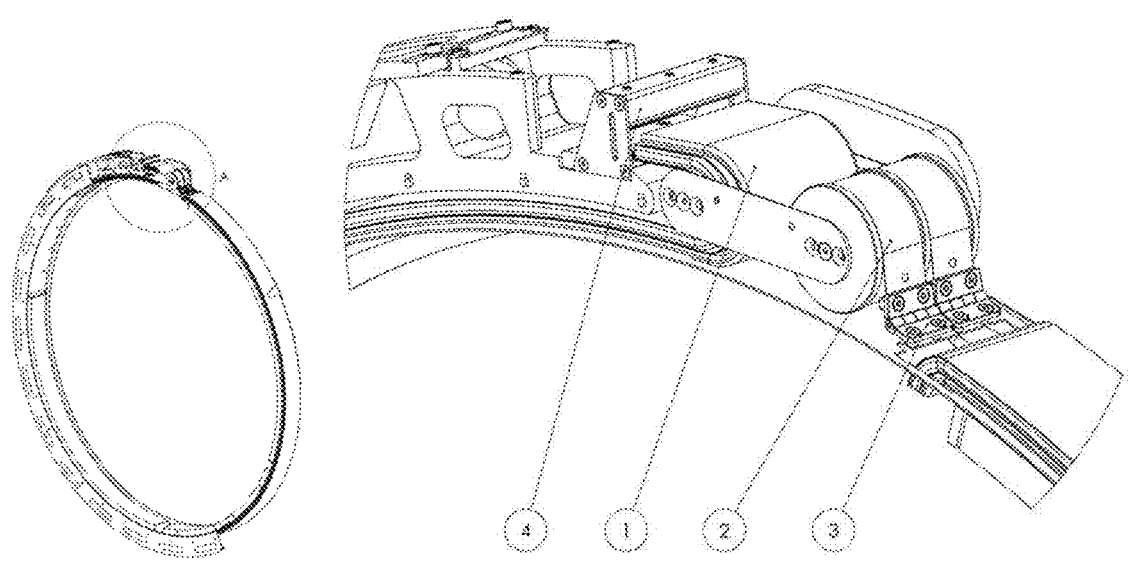

FIG. 14 shows an embodiment having a cable guidance with constant force spring and an enlarged view thereof. The cable guidance includes a flat cable loop 1, constant force roller springs 2, a mounting point of springs 3 on the inner stationary ring, and clamping 4 of flat cables on the rotating arm.

Figure 15:
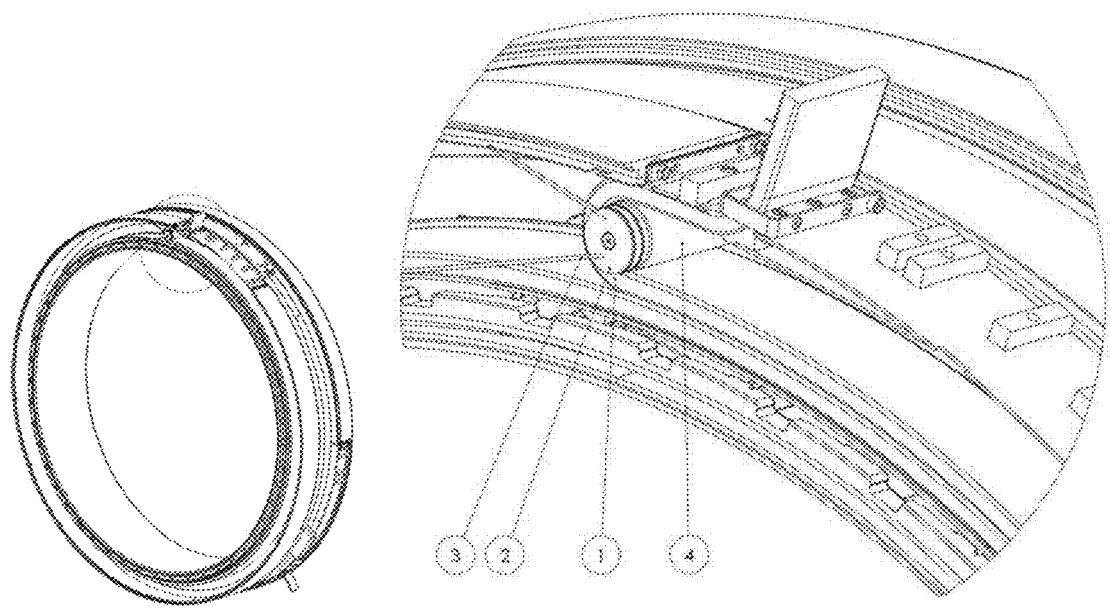

FIG. 15 shows an embodiment having cable guidance with a rope in a view similar to FIG. 14, including flat cables 1 at a loop, an idler 2 with groove for tensioning the rope, a tensioning rope 3 laterally to a flat cable space, and an optional idler pulley 4.

Figure 16:
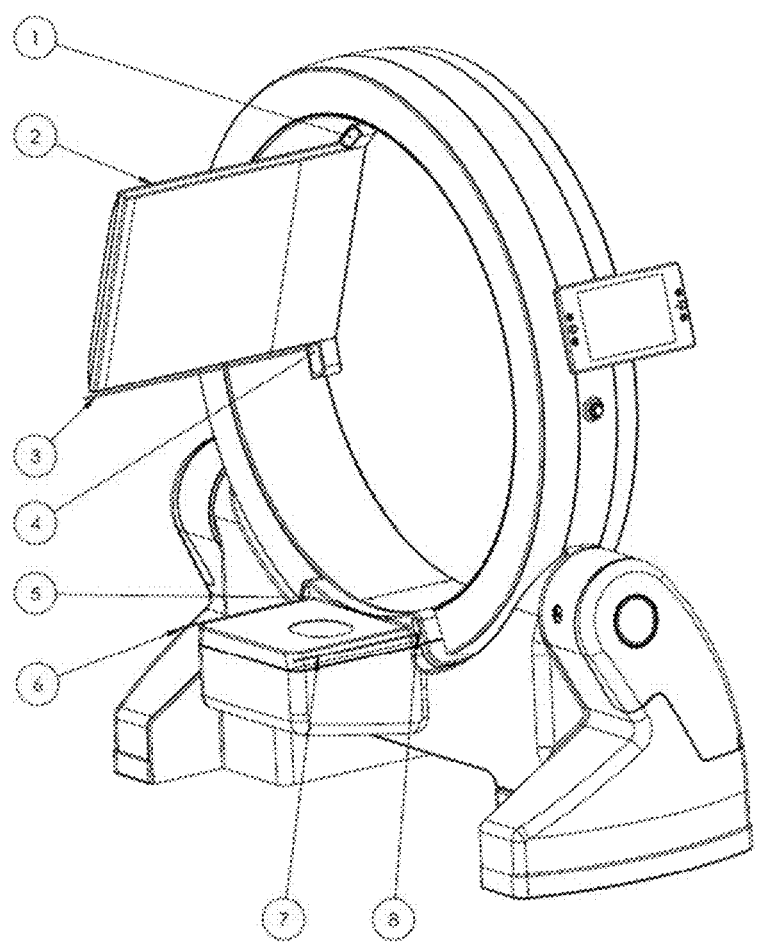

FIG. 16 shows an embodiment of the imaging ring system with laser distance sensors. The system is provided with exit windows 1 and 4 for a laser distance sensor on the detector, sensing laser lines 2, 3, exit windows 5 and 8 for a laser distance sensor on the X-ray arm, and sensing laser lines 6, 7. The distance sensors are used to stop motion of moving objects if occluded by an obstacle for collision protection.

Figure 17:
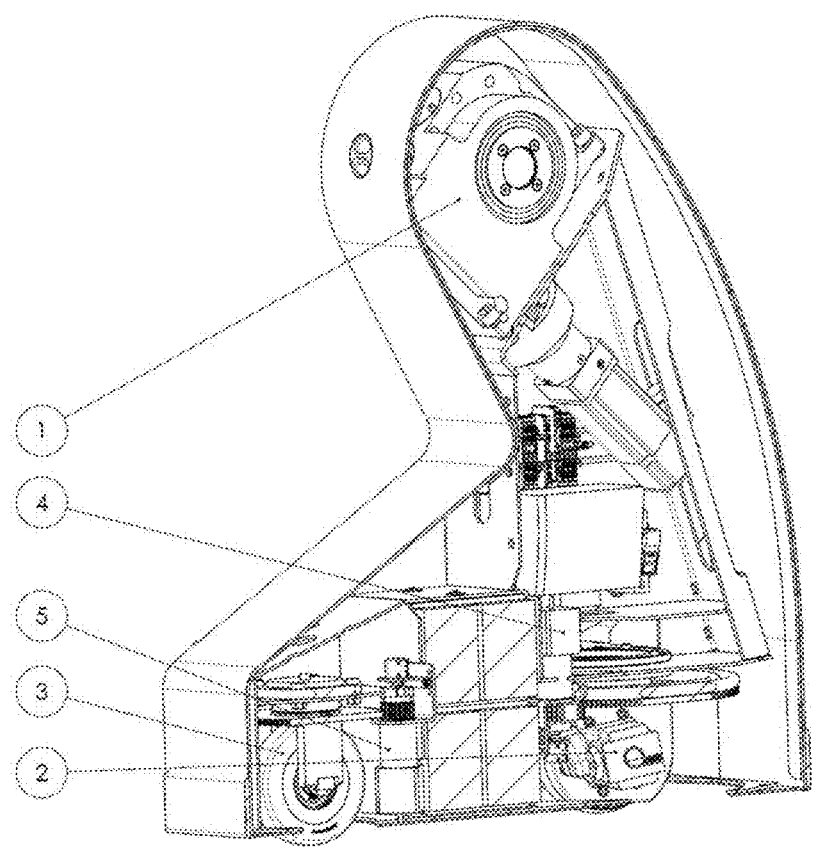

FIG. 17 more specifically shows a leg according to an embodiment that may be used with the system according to the present invention. The leg includes a gear box hip joint 1, preferably including a motorized gantry tilt with a worm accessible from the top for emergency maneuvers, a motorized and steerable rear drive unit 2 at the heel, a steerable front wheel 3 at the toes with load sensor, a steering motor 4 for rear drive at the heel, and a steering motor 5 for the front wheel.

Figure 18:
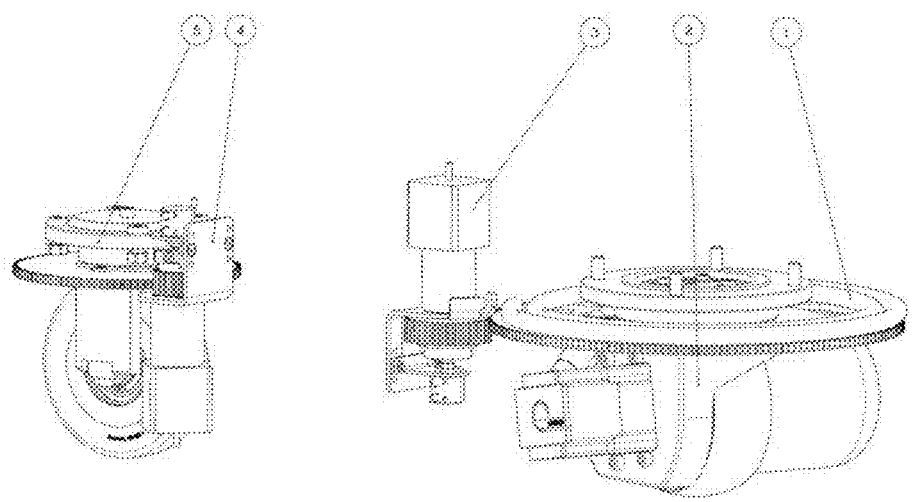

FIG. 18 shows in more detail front and rear wheels that may be used in a leg, such as shown in FIG. 17. The wheels include a cable spiral 1 on top of the rear steering gear wheel to power the drive servo motor, a fork 2, a rear steering motor 3, a front steering motor 4, and a load sensor 5.

Figure 19:
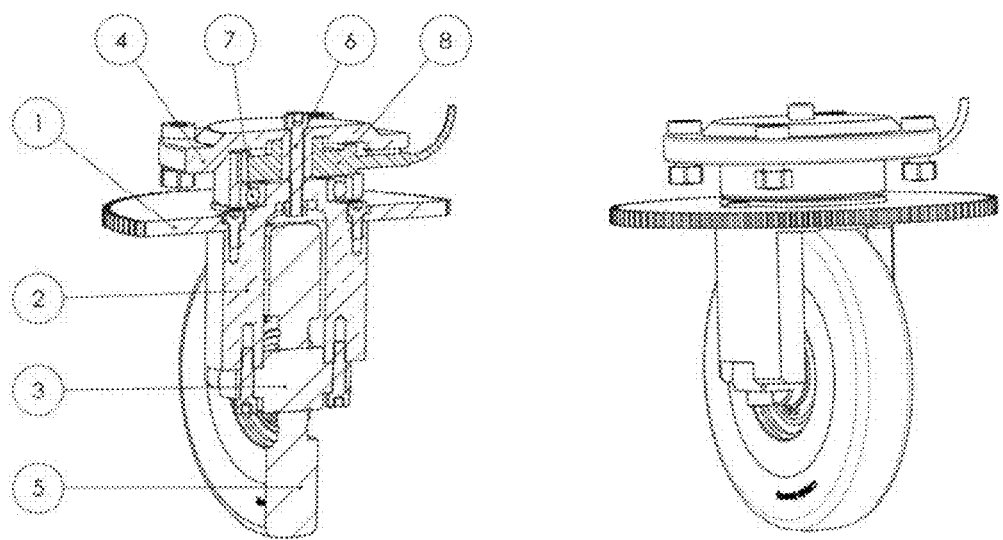

The front wheel is shown in more detail in FIG. 19, illustrating a gear wheel 1 used for steering, a fork 2, a axle 3, a washer 4 for attaching the wheel to the leg, the wheel 5, a countered screw 6 to adjust play allowing to adjust the steering angle in a manual emergency operation, a bearing 7, and load sensor 8.

Figure 20:
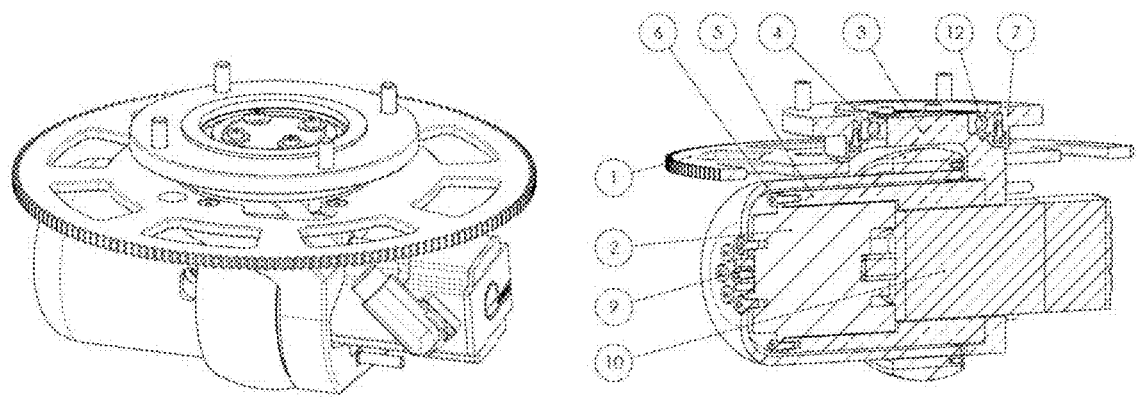

FIG. 20 gives a more detailed illustration of the rear drive unit with a gear wheel 1 controlling the steering angle, a planetary gear 2, a (lefty) fork 3, a wheel 4, an adapter 5, a hollow shaft 6, a mounting washer 7, a gear box mounting 9, and a servo motor 10 with brakes.

Figure 21:
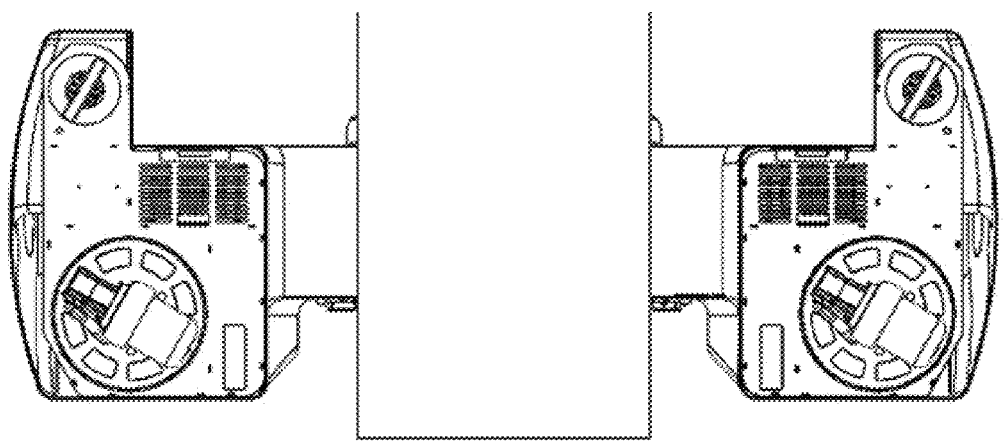

FIG. 21 schematically shows a bottom view of the four wheels of the mobile imaging ring system according to an embodiment of the present invention wherein, by adjusting all four wheels essentially parallel, a translation of the system on the floor can be achieved in any direction.

Figure 22:
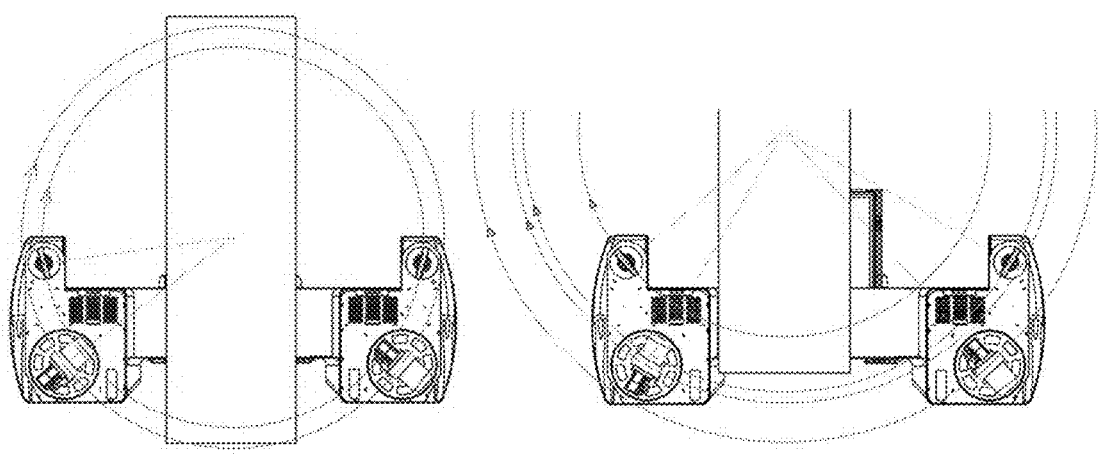

FIG. 22 shows a view similar to that shown in FIG. 21, wherein the wheels are oriented to allow an isocentric rotation, i.e. about centered object (left figure) and an eccentric rotation, i.e. about the ff-centered imaging center (right figure).

Figure 23:
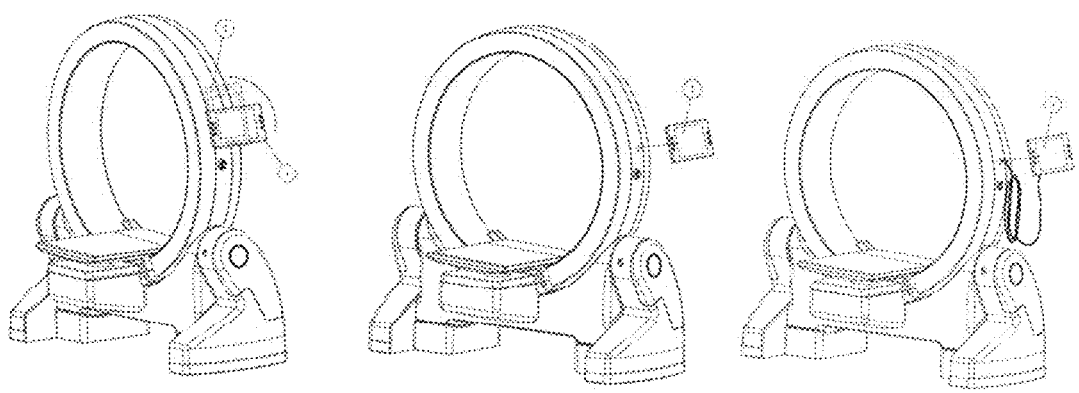

FIG. 23 shows a hand held HMI docking attached to the system of the present invention. The left figure shows a touch screen tablet in landscape orientation 1 and portrait orientation 2. Generally, any inclination is adjustable for improved usability when gantry is tilted. The middle figure shows that the touch screen 1 can be undocked from the gantry for wireless remote access to the motion control system and remote irradiation, wherein docking (charging) is possible on left and right side of gantry on outer stationary ring. In the right figure, HMI tablet 1 is shown that can be wired and connected to the stationary outer ring when no wireless connection is possible.

Figure 24:
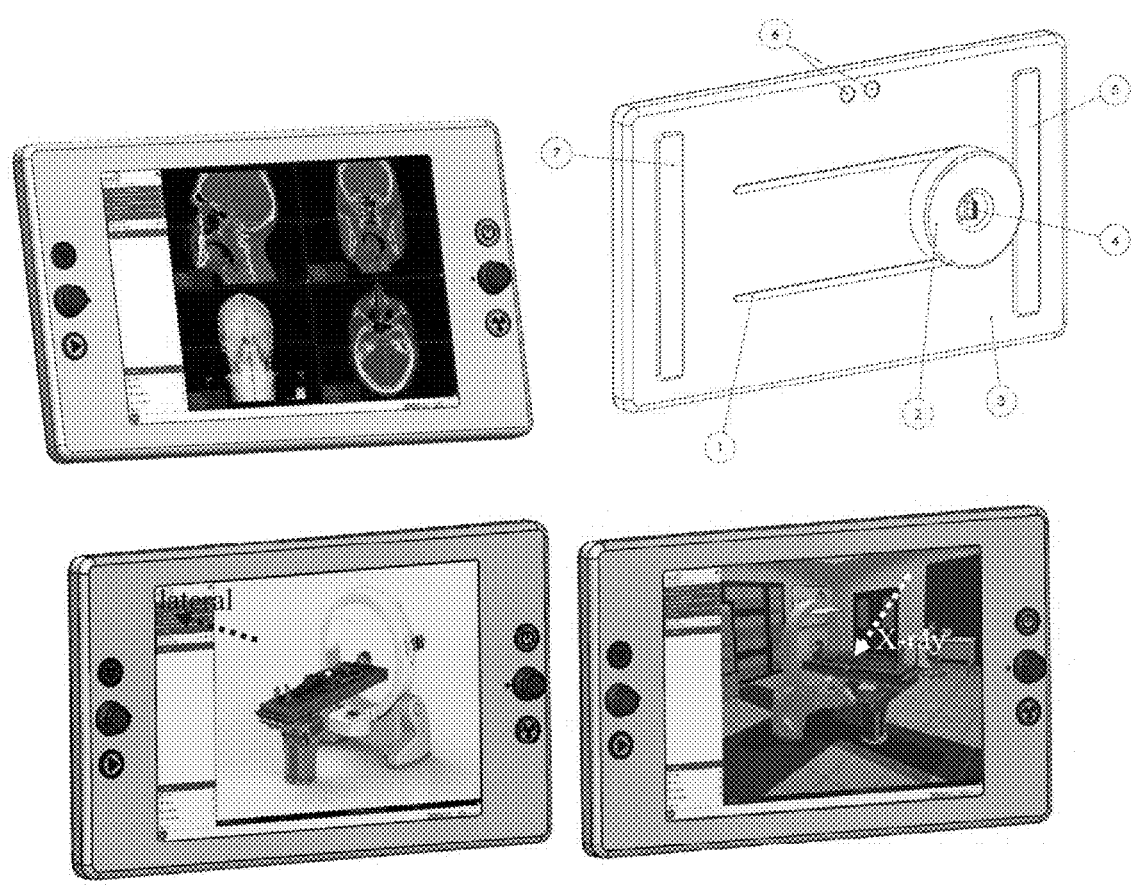

FIG. 24 provides a more detailed view of the hand held control (HMI). The top left figure shows a touchscreen remotely displaying anatomical images (volumes and projections) inline, in real time, during acquisition and inline reconstruction on the hand held HMI operated from a radiation protected area. The top right figure shows a rear view of tablet with guiding means 1 to move the docking point left or right, depending on left or right mounting on gantry, a, preferably pivoting, docking point 2, a HMI tablet frame 3, a connector that may be internally rotatable, to connect the HMI with the ring, to a power line to charge the accus, to a signal line and to a LAN, a deadman switch 5, and cameras 6. The cameras are shown symbolically, there may be a single camera or a pair of stereoscopic cameras. The bottom left figure illustrates that for motion control, the flat touch screen user interface offers visualisation of ring and movable components together with orientation of patient (avatar or 3D surface scan). This supports manual movements, for example the adjustment of an imaging center with respect to a patient, by means of graphical user interface, joystick(s) and buttons in frame. The axis to be moved can be depicted (object selected, direction and maximum velocity adjusted) by the user, the motion can then be directed by joysticks; the axis can be a physical axis (such as source angle) or a combined motion of multiple axis (e.g. moving synchronously in robotic motion along a preplanned trajectory). The bottom right figure illustrates that the cameras at the rear side of the touch tablet can be used by the operator to film the scene in an OR, to register the actual 3D orientation of the imaging system with respect to the patient, to set an imaging center and X-ray direction on the filmed scene in the picture displayed on the graphical user interface, and then to actually move the robotic system to the planned imaging position in real world by one button click. For example, augmented reality may be used, the depicted arrow shows the desired imaging center and the direction of X-ray. The robotic trajectory may be automatically calculated (inverse kinematic).

The relative orientation of the user with respect to the system is important for joy stick functionality from a usability perspective. For example, moving a joystick to the right moves the imaging center to the right if viewed from begind the gantry. If the user stands in front of the gantry, moving the joystick to the right would (intuitively) result in a translation of the system to the left (viewed from behind). Same works for rotations of source and detector: a clockwise (cw) rotation of joystick in a cw direction would result in a positive or negative rotation, depending on the viewpoint.

Figure 25:
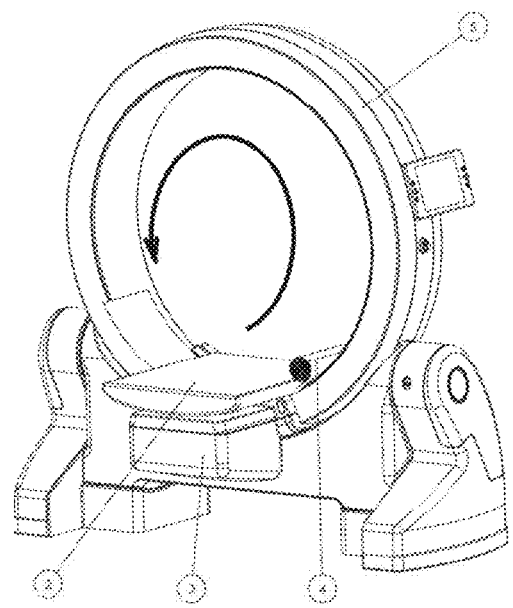
Figure 25:
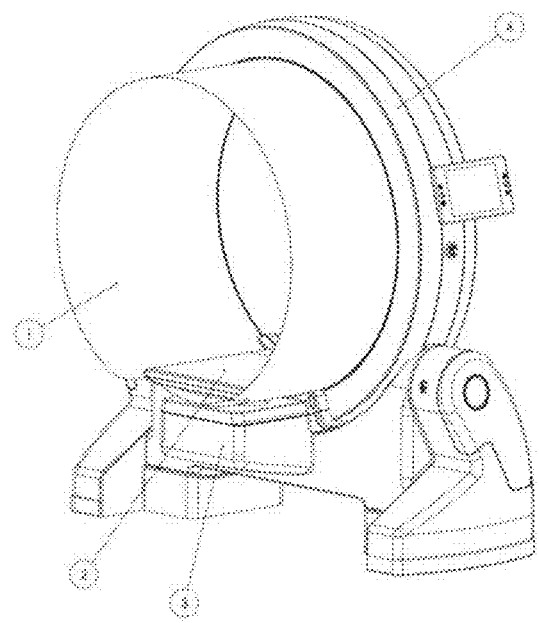

FIG. 25 illustrates the sterility concept to be applied to the system according to the invention. The left figure shows a solution using draping including a sterile bag 2 to cover the detector arm, the source arm 3, the roller 4 with sterile foil to cover the bore, and ring gantry 5. The right figure shows a tunnel solution including a tunnel 1 of thin plastic foil, that preferably is radiotransparent and translucent, wherein the detector arm 2 may be additionally draped. Furthermore, the source arm 3 and ring gantry 4 are shown.

FIGS. 26 to 29 illustrate various setups to be used for specific types of examination.

Figure 26:
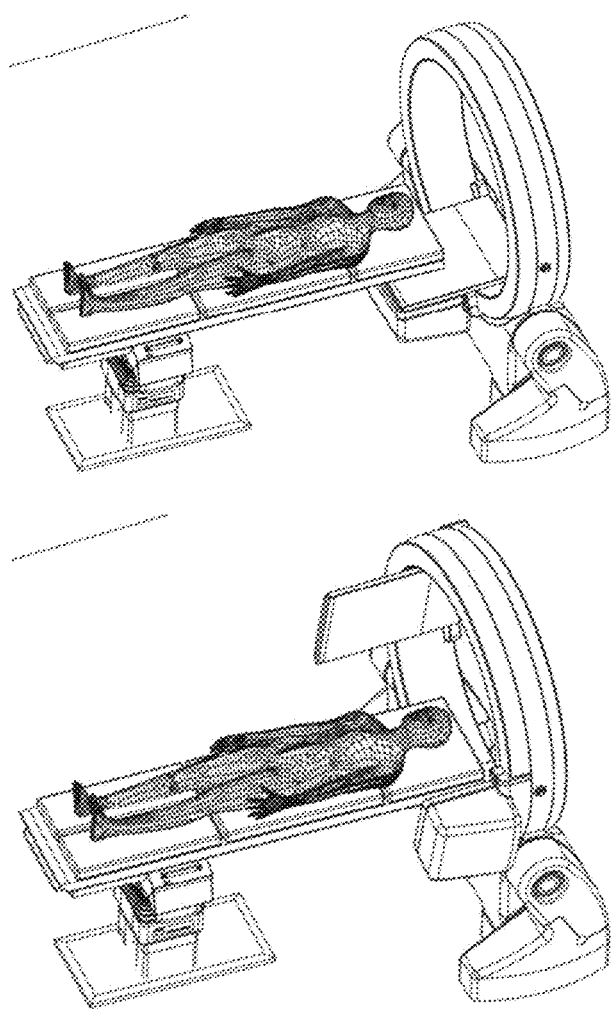

FIG. 26 shows imaging on a cantilever OR table in the parking position (upper figure) and the imaging position when imaging the head of the patient. Note that no adjustments in table height or lateral position is required in the non-isocentric image acquisition protocols.

Figure 27:
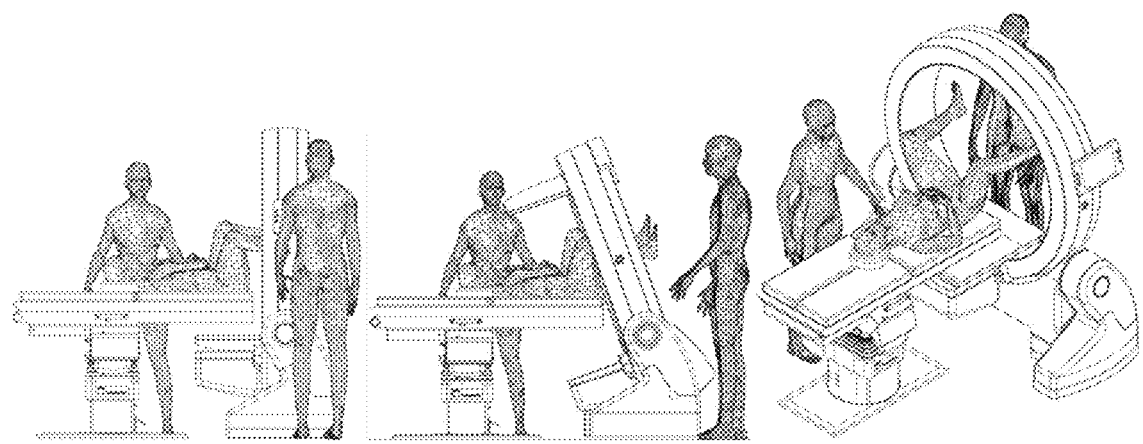

FIG. 27 shows imaging in Brachytherapy including the insertion of a gynecological or rectal applicator with image guidance.

Figure 28:
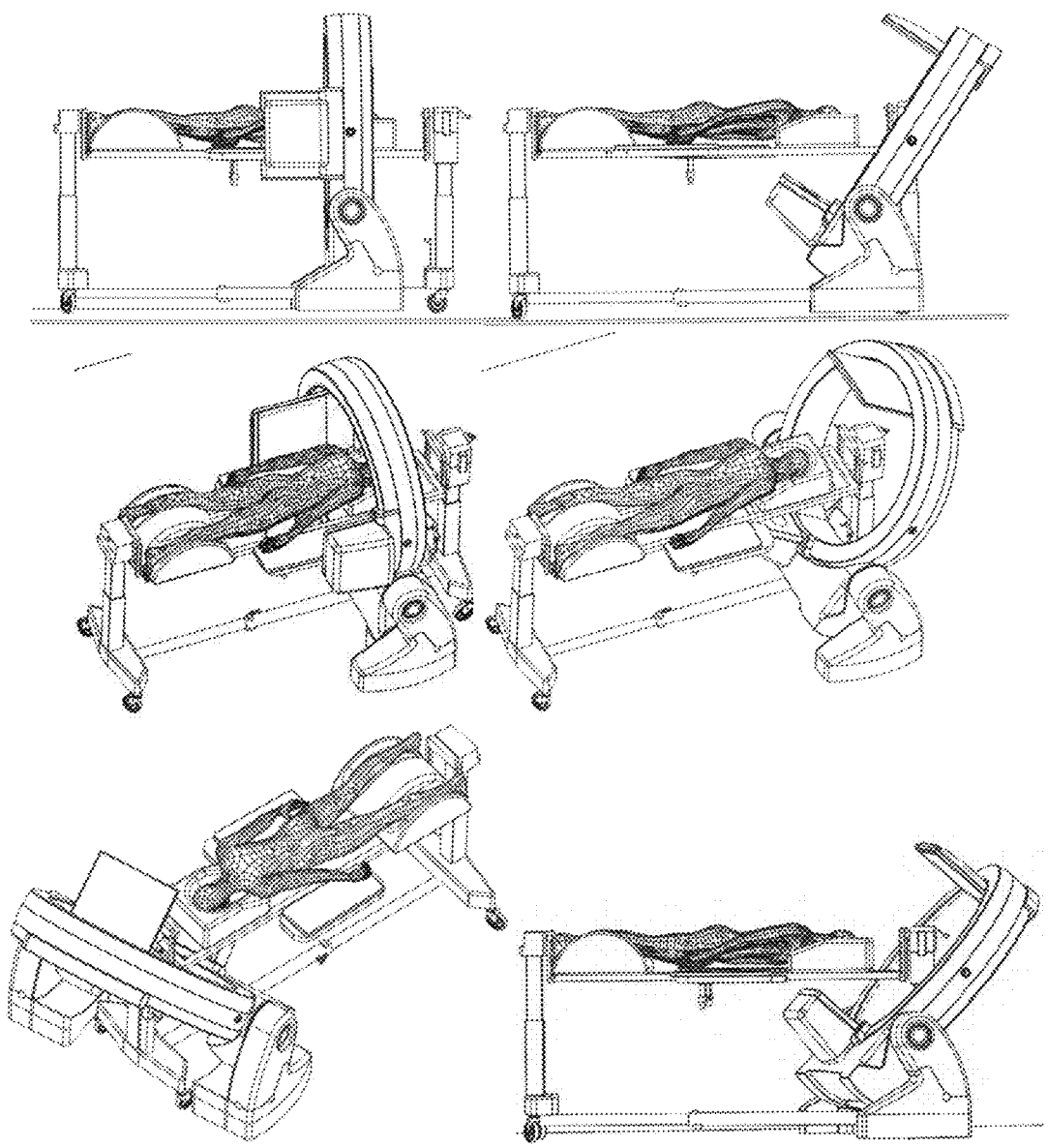

FIG. 28 shows an OR setup with a Jackson table, the top left figure showing the imaging system in imaging position (spine), the top right figure showing the imaging position in the parking position, to open the space for the medical team during the intervention and reduce requirements to sterilizing gantry and arms during surgery. Robotic motion from the parking position to the imaging position (and back) can be preplanned, teached in (recorded) and (re)played. The bottom perspective figures illustrate that the ring gantry can also be rotated on the floor and the gantry can be tilted in the parking position to open a wider space for surgeon with access to patient.

Figure 29:
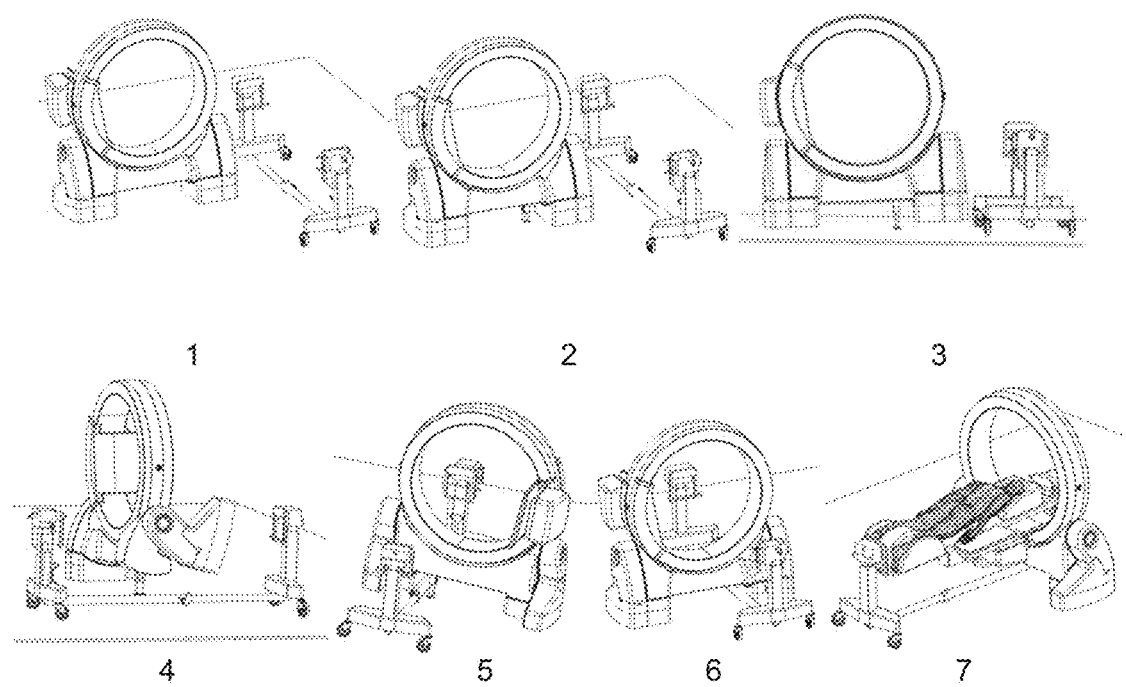

FIG. 29 show the preparation of the OR with the Jackson table with the following steps: step 1 position Jackson table next to mobile imaging system, step 2 extend actuator in supporting structure, step 3 lift imaging system on one side, step 4 rotate the lifted leg to open space for the Jackson beam above floor, step 5 position Jackson table with beam underneath supporting structure, step 6 retract actuator into support structure, and step 7 position table top and patient for OR.

Figure 30:
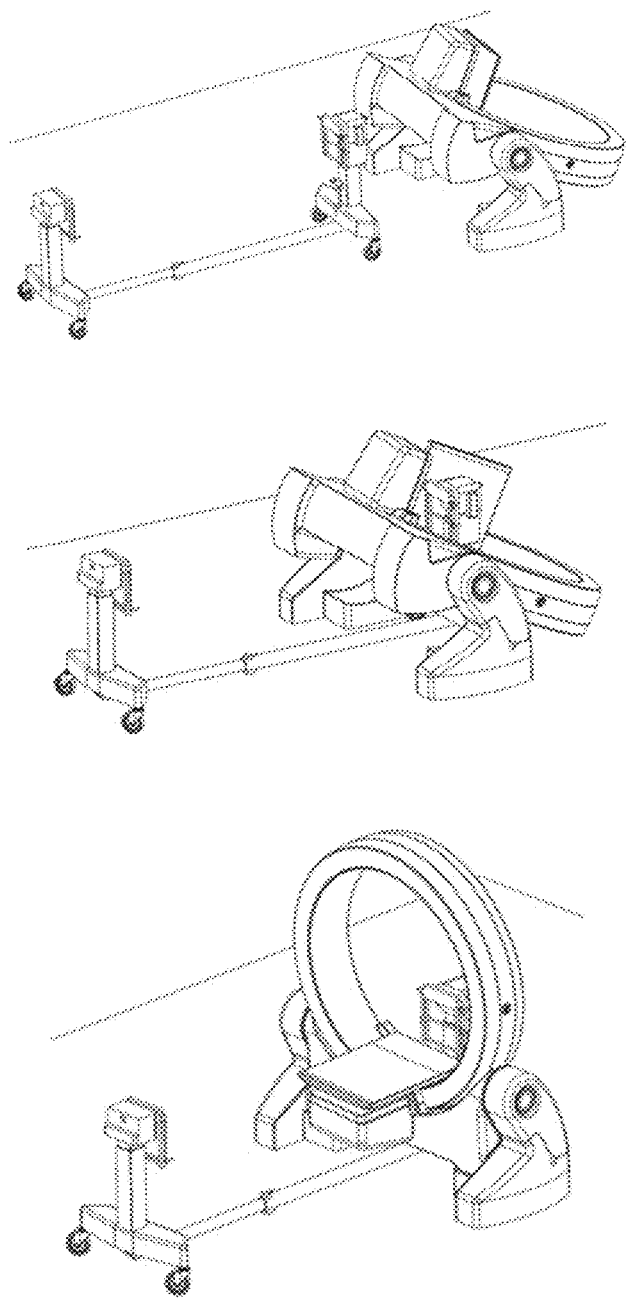

FIG. 30 shows an alternative Jackson setup. In the top figure, the gantry is tilted in positive direction (e.g. +100°) until it almost reaches the floor, in the middle figure, the Jackson table is inserted with lowered column (detector rotated laterally), and in the bottom figure the gantry is rotated in the upright position (e.g. 0° tilt) and prepared for patient setup.

Figure 31:
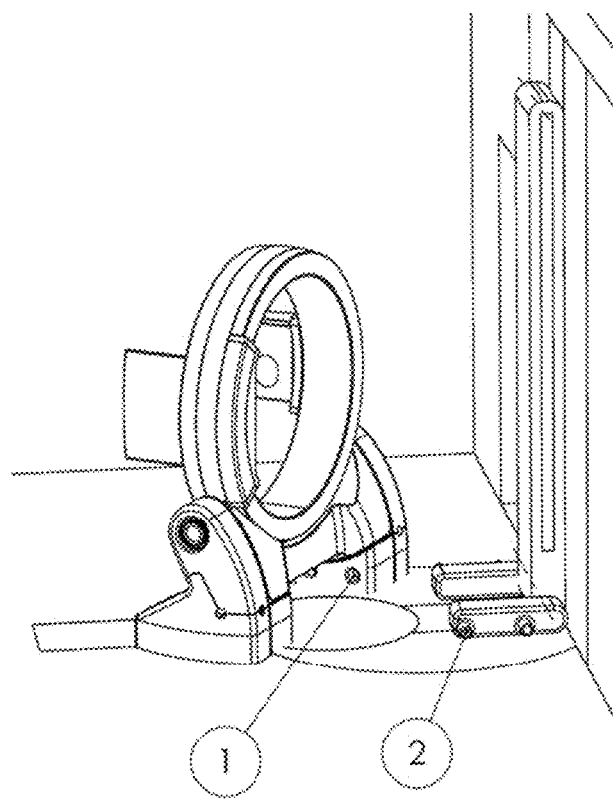

FIG. 31 shows the docking of the mobile imaging system of the present invention to a carriage on a rail structure (elevator). For docking, docking grooves 1 at inner sides of legs and docking bolts 2 and docking arms may be provided, which are rotatable (pivoting) on carriage, which is guided by rails, which inclination can be adjusted at any angle from vertical to horizontal.

Figure 32:
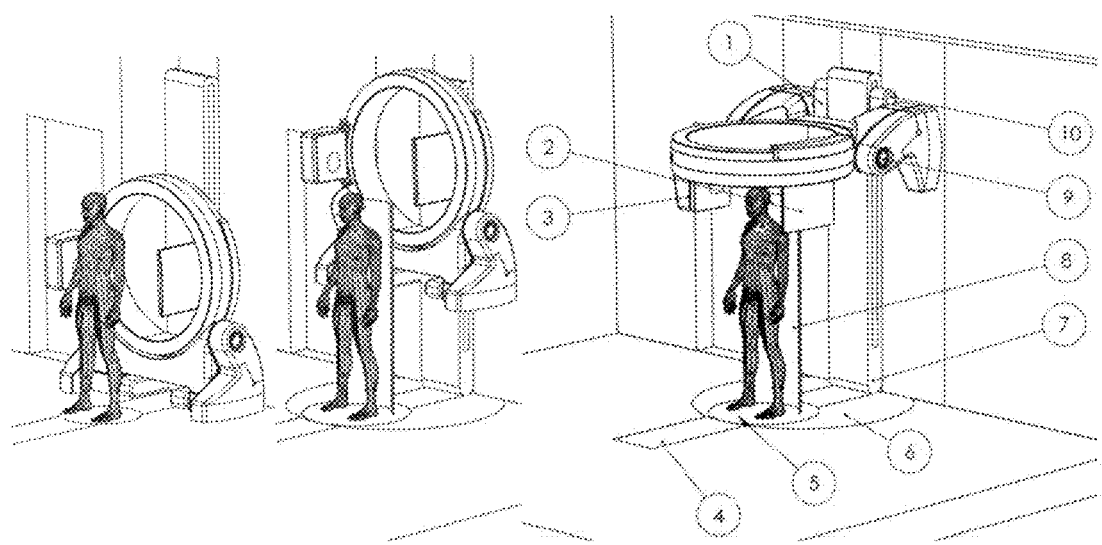

FIG. 32 illustrates the setup for use in a vertical scan, the patient standing upright. In the left figure, the mobile Imaging systems docks to carriage on rails. The middle figure shows the mobile imaging system being lifted by elevator. In the right figure, the mobile imaging unit is tilted by a motor on the carriage and translated alongside of the rails to perform a scan, e.g. a helical scan. The system shown in FIG. 32 includes docking arms 1, a detector 2, and a source 3. Markings on the floor include a marking 4 to indicate the range of motion of rails if tilted from vertical over inclined to horizontal position, a marking 5 to indicate scan FOV or a rotating platform, as can be used in particle therapy, in order to rotate the patient with respect to the incident treatment beam the rotating stage may carry a bed or a seat or a board or a combined patient positioning system to provide a fixation for the patient during treatment and means for alignment of patient with respect to the treatment beam), and a marking 6 to indicate position of mobile imaging unit for docking maneuver. The system further includes elevator rails 7 with an adjustable inclination, an indexed fixation board 8 for patient setup devices, preferably radiotransparent, a gantry tilt axis 9, and a rotation axis 10 of docking arms on carriage.

Figure 33:
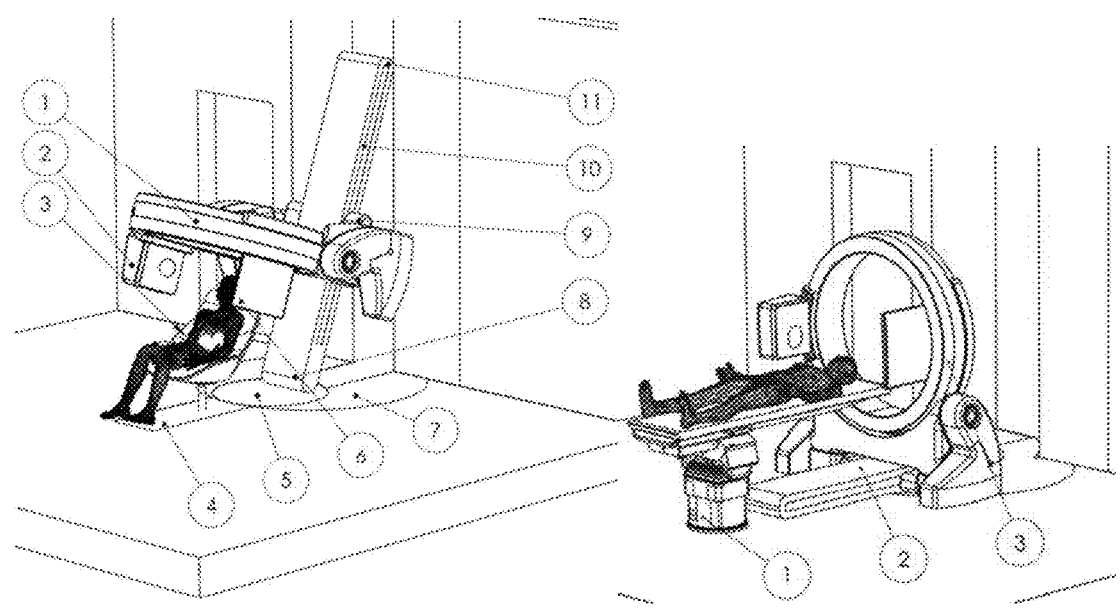

FIG. 33 show the setup used in an inclined scan wherein the patient is in a seated or a lying position. The left figure shows an inclined scan, the system including a ring gantry 1, a source 2, a seat 3, a marking 4 on the floor to indicate the area of motion for rail structure (position in horizontal scan orientation), a marking 5 on the floor or a rotating stage, a detector arm 6, a marking 7 on the floor or a second rotating stage, supporting wheels 8 or a docking point on a horizontal carriage on the rails for an inclined rail structure to allow adjustment of inclination, docking arms 9 on the carriage on the rails with adjustable inclination, rails (elevator) 10, and a docking point 11 on a vertical carriage on a vertical drive unit to support the rail structure on wall. The right figure illustrate a horizontal scan, with a patient table 1, a rail structure 2 in a horizontal position, and a docked mobile imaging system 3.

Figure 34:
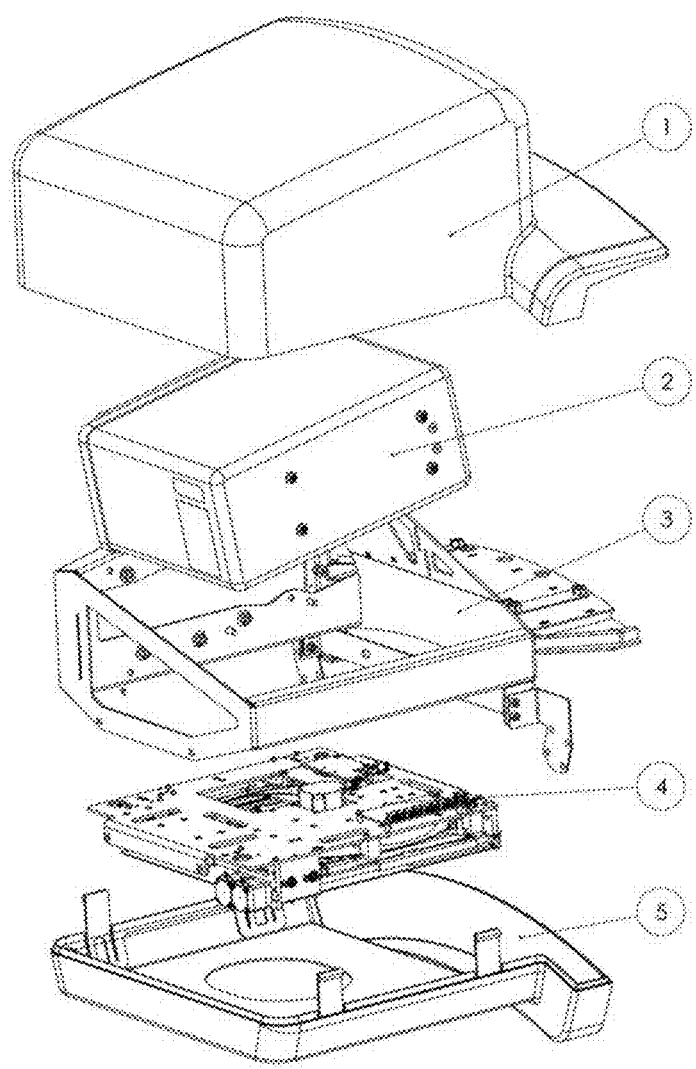

FIG. 34 shows an exploded view of the source arm according to an embodiment to be used with the system of the present invention. The source arm includes an outer source arm cover 1, an inclined X-ray source 2, exemplarily including a monotank, an oil filled, rotating anode, with integrated high voltage generator, primary aperture and optional flattening filter, a source arm 3, a collimator 4, preferably with 4 independently moving jaws, carriage, filter wheel, and line lasers, and an inner source cover 5, e.g. with an exit window for X-ray beam, laser distance sensors, line lasers, and cameras.

Figure 35:
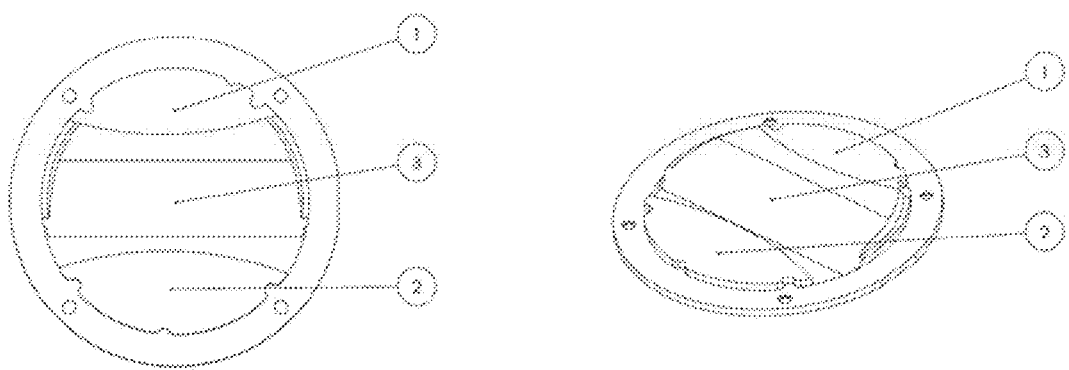

FIG. 35 shows a primary aperture and flattening filter according to an additional aspect of the present invention. The aperture includes X-ray collimation (tungsten, led) 1, 2, and air or aluminum flattening 3 to compensate for the X-ray anode's self attenuation Heel effect. The primary aperture may be mounted directly to the exit window of the X-ray tube, upstream, as close as mechanically possible to the focal spot in order to reduce the amount of out-of-focus-radiation from tube reaching patient and detector. The primary aperture is wider in lateral direction (>60°) than longitudinally (superior inferior about <20° at central axis) in order to support variable detector offsets and maximal FOV. The bent shape at superior and inferior border models the projections to all possibly allowed off-centered detector positions.

Figure 36:
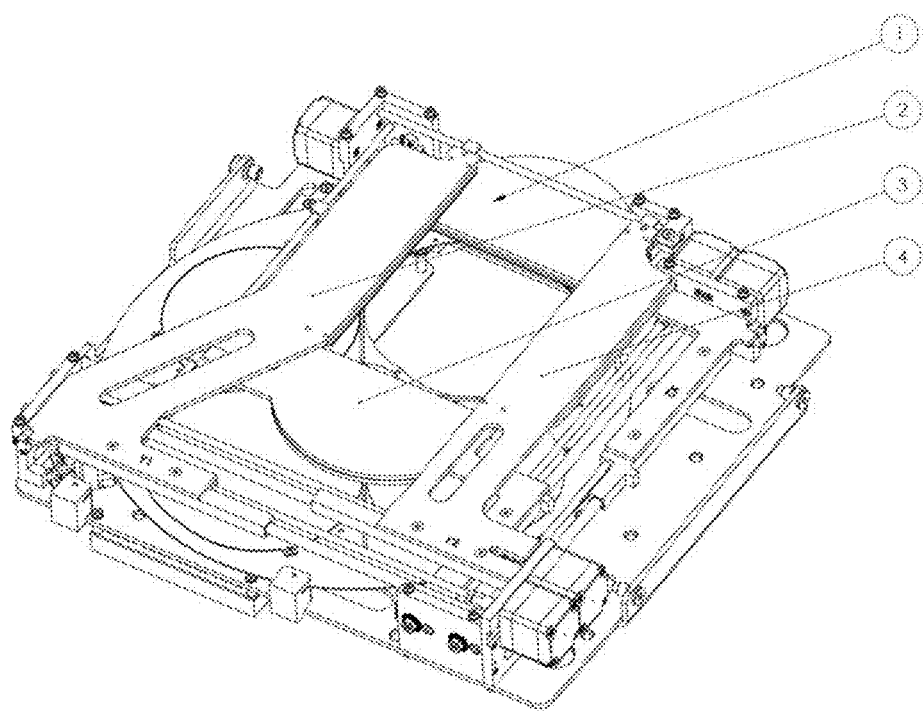

FIG. 36 shows a detailed view of independently moving collimator jaws that may be used in the system of the invention, in particular an x2 jaw 1 (according to IEC 61217 coordinate systems, scales and conventions), a y1 jaw 2, an x1 jaw 3, and a y2 jaw 4. All collimator jaws can be moved independently and have a large overtravel to allow fan beams (collimation of X-ray beam to slit) to travel over the FOV (CT application).

Figure 37:
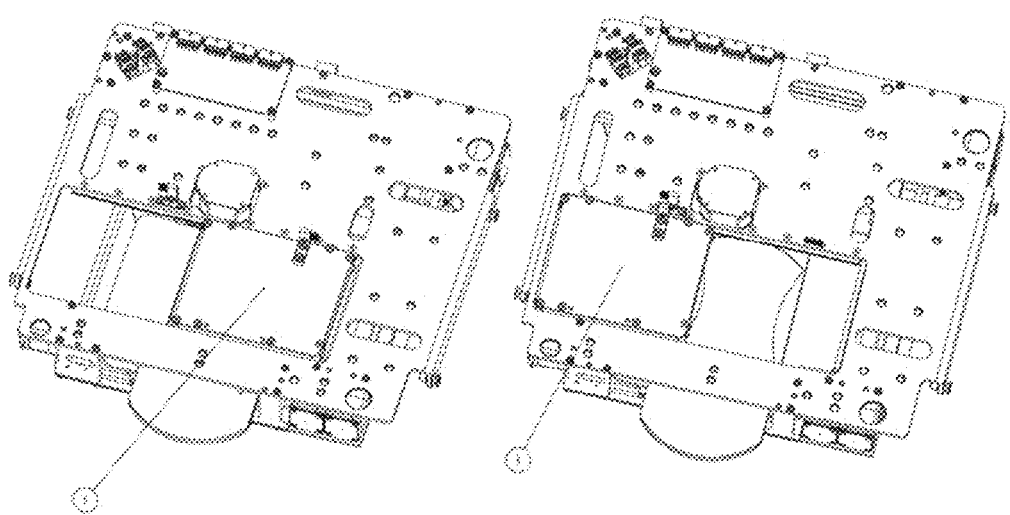

FIG. 37 shows a filter carriage that may be used in front of the radiation source. The left figure shows the filter carriage in foremost position inserted in X-ray beam, the right figure shows the filter carriage in retracted position (open beam). The filter carriage can be used to position a bow tie filter or, more generically, a three dimensionally shaped attenuator in any intermediate position to modulate the X-ray flux or to insert different bow tie filters optimized for different FOVs.

Figure 38:
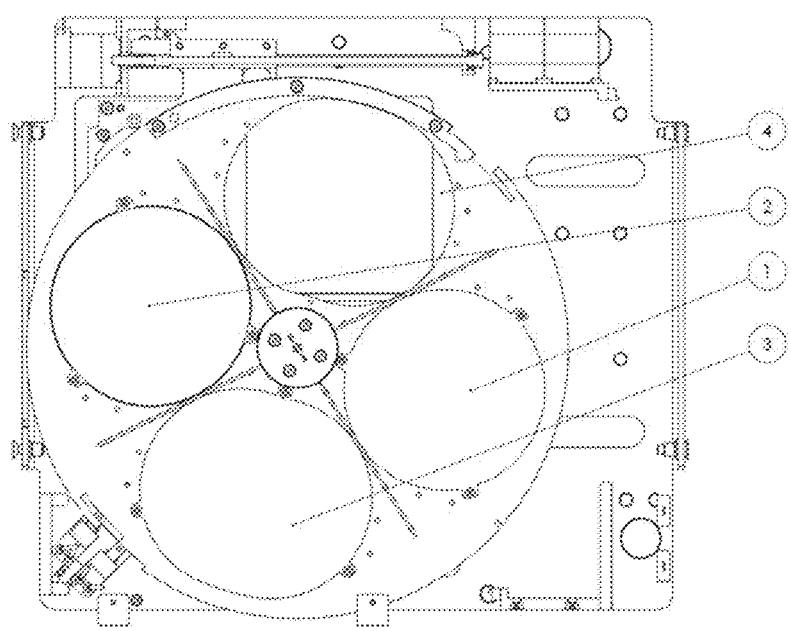

Alternatively, or in additional, a filter wheel as shown in FIG. 38 may be applies on the collimator with beam hardening inserts, such as an aluminum insert 1 (beam hardening to increase the tube's inherent filtration), a copper insert 2 (to remove more of the low energy photons, e.g. for pediatric imaging), an enlarged sector 3 with compound silver copper insert (for dual energy applications in pulsed mode), and an enlarged sector 4 with no insert (air), and counter balanced (for dual energy applications in pulsed mode).

Figure 39:
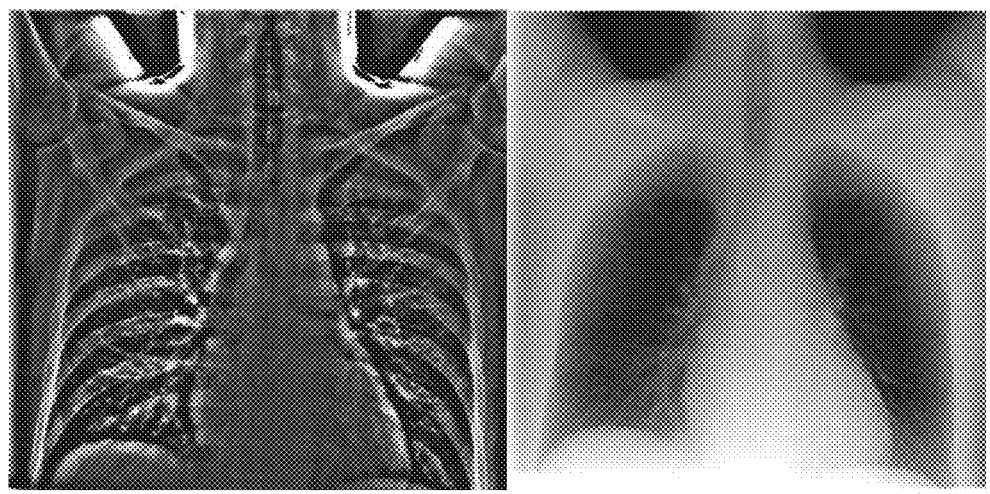

The system according to the invention also allows for dual energy imaging, the result being exemplarily shown in FIG. 39. The left figure show a bone enhanced image whereas the right figure shows a soft tissue enhanced image (ribs being removed as occlusion, e.g. for enhanced tracking applications in radiation therapy of peripheral lung cancer).

Figure 40:
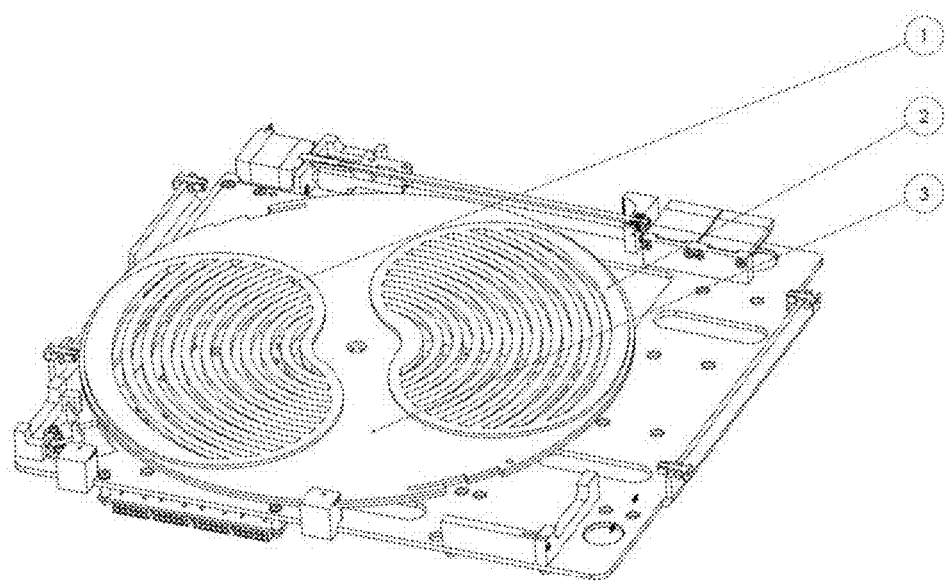

FIG. 40 shows a filter wheel on a collimator with BSA, including tungsten inserts 1, 2, with circular slits, and a transparency about 50%, providing alternating beam blockers if rotating synchronously with X-ray pulses. Furthermore, a rotating filter wheel 3 is shown.

Figure 41:
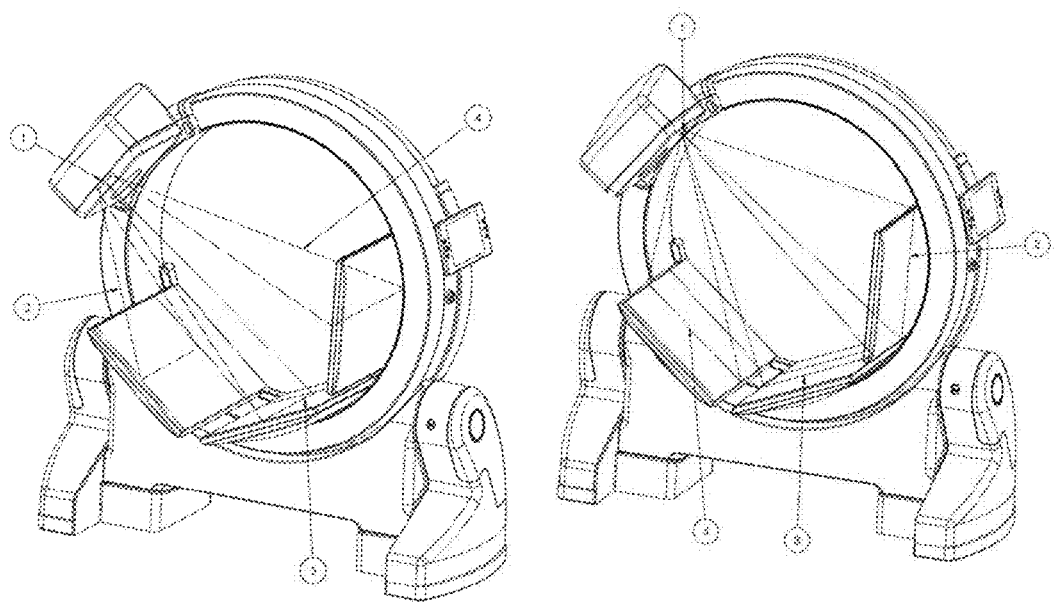

FIG. 41 illustrates the use of a pair of line lasers with the collimator to project a cross hair. In the left figure, a rail 1 with a carriage and a pivoting line laser and laser lines 2, 3, and 4 projected in the center of the X-ray field, centrally on detector, i.e. in a longitudinal imaging plane, are shown. The right figure shows a stationary line laser rigidly attached to sourceans line projections 2, 3, and 4 on different detector offset positions. i.e. in a transaxial imaging plane.

Figure 42:
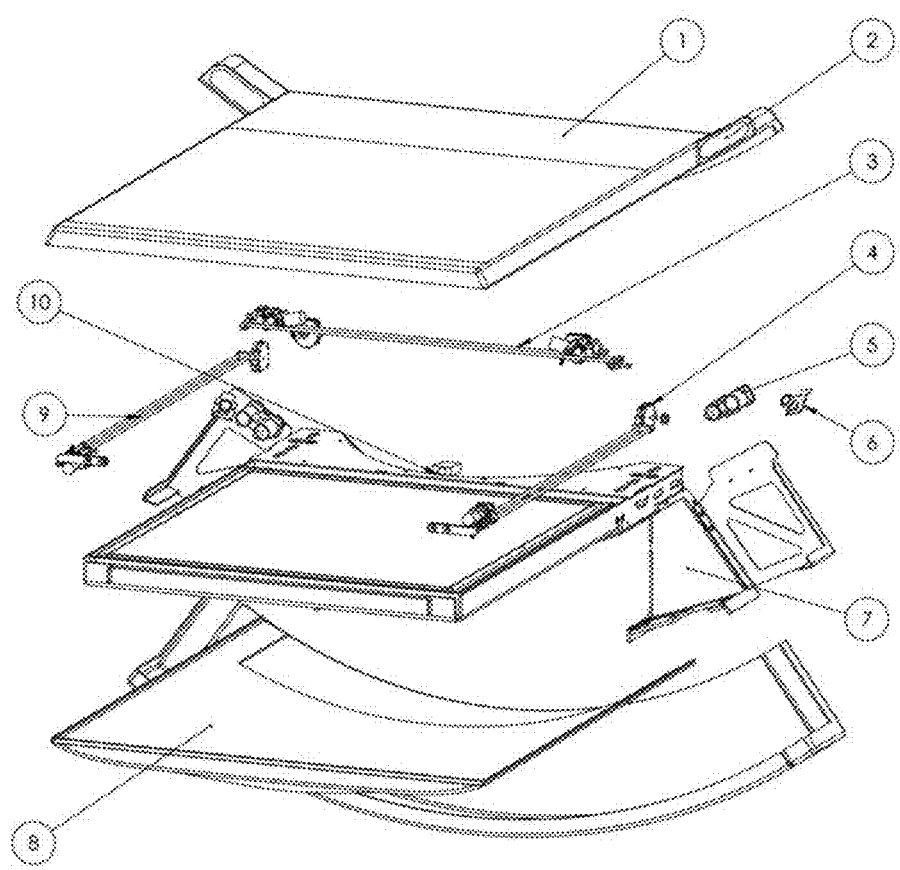

FIG. 42 shows an exploded view of a detector arm used according to an embodiment of the invention. The laser arm includes a, preferably translucent, front cover 1, a window 2 for laser distance sensors and stereoscopic cameras, rails 3 for two carriages with drive units and line lasers (x jaws), a rail 4 for a carriage with a drive unit and a line laser (y1 jaw), a laser distance sensor 5 for collision protection, a stereoscopic camera 6, a folded detector arm 7 attached to outer ring on the gantry, an outer detector cover 8, a rail 9 for a carriage with a drive unit and a line laser (y2 jaw), and video projector 10, providing structured light for surface scanning, backprojection, or augmented reality applications.

Figure 43:
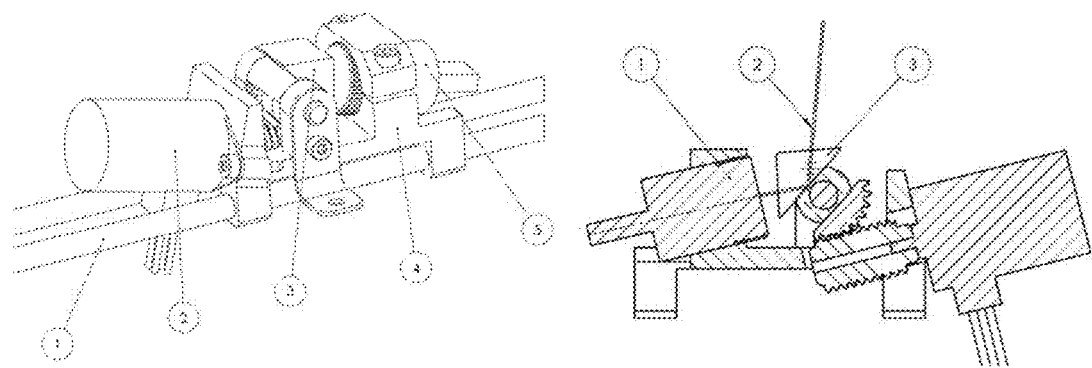

FIG. 43 shows movable line lasers, including, as shown in the left figure, rails 1, a stepper motor 2 with a worm gear to drive the rotation of an optical prisma, an optical glass prisma 3 to mirror and direct the laser line in the direction of the X-ray focal spot, a carriage 4, and a laser 5 with cylindrical lens to emit a laser line. The right figure provides a mirrored view, showing a line laser 1, a plane of laser light 2, and an optical glass prisma 3.

Figure 44:
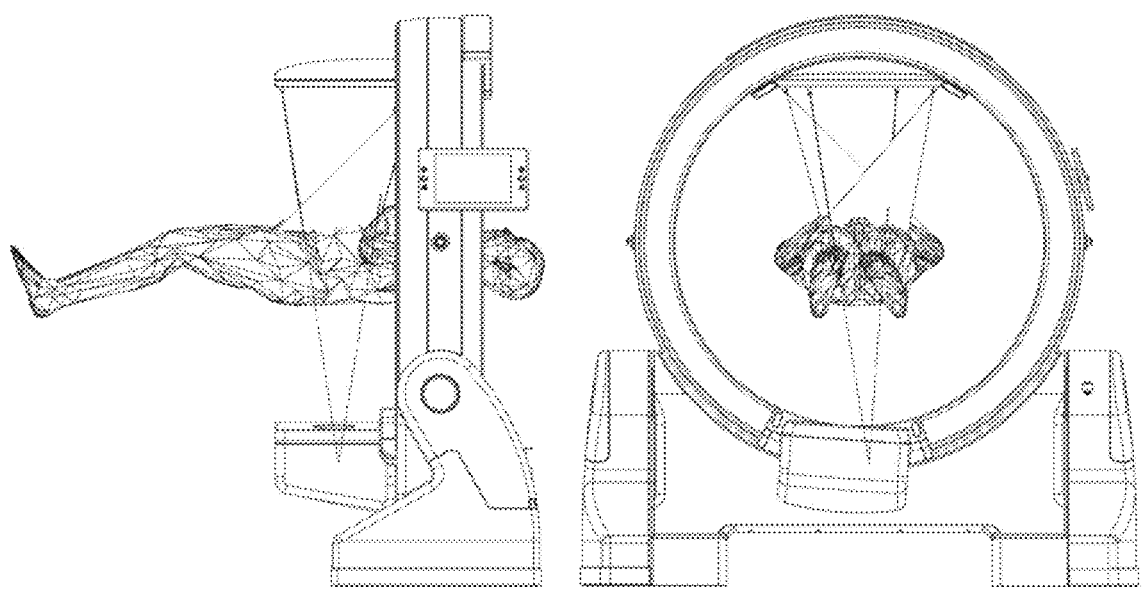

FIG. 44 illustrates an inverse projection of X-ray field or central axis, i.e. the imaging center, wherein four individually movable line lasers on detector side are used to project the X-ray field exit onto the skin of the patient (planar FOV or 3D cylinder). If two orthogonal line lasers are turned on, the currently set field center (and the imaging center) can be projected onto the skin as a cross hair. If two parallel line lasers are turned on, the longitudinal length of 3D FOV can be projected. Moving line laser projections on skin of patient can also be used for surface scanning in combination with one or more cameras on detector, source or inner ring of gantry.

Figure 45:
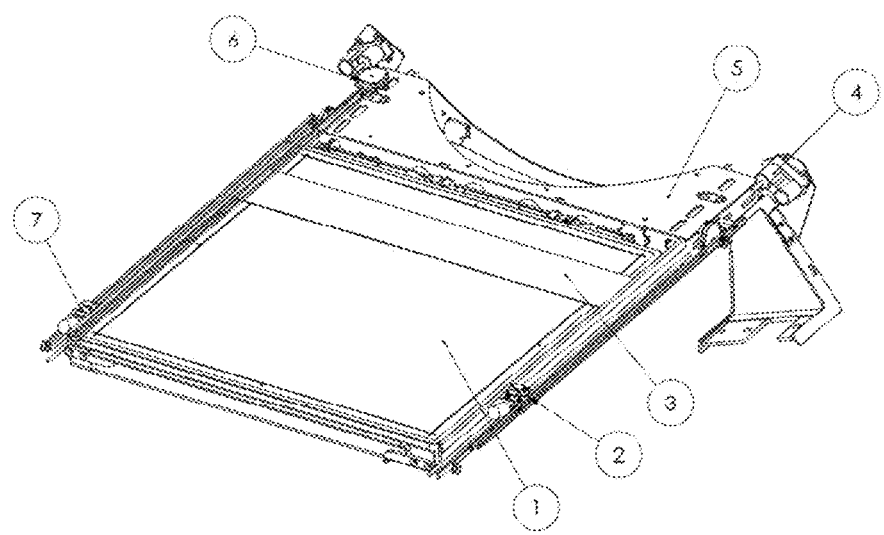

FIG. 45 shows a movable anti scatter grid that may be used with the system of the present invention, the figure shown in the active area 1 of a flat panel detector, rails 2 for carriages, a movable scatter grid that preferably covers a portion of detector entrance area sufficiently large enough for slit or fan beams or helical scans, a laser distance sensor 4, detector arm 5, a drive unit 6 for the belt driven anti-scatter grid, and movable lasers 7.

Figure 46:
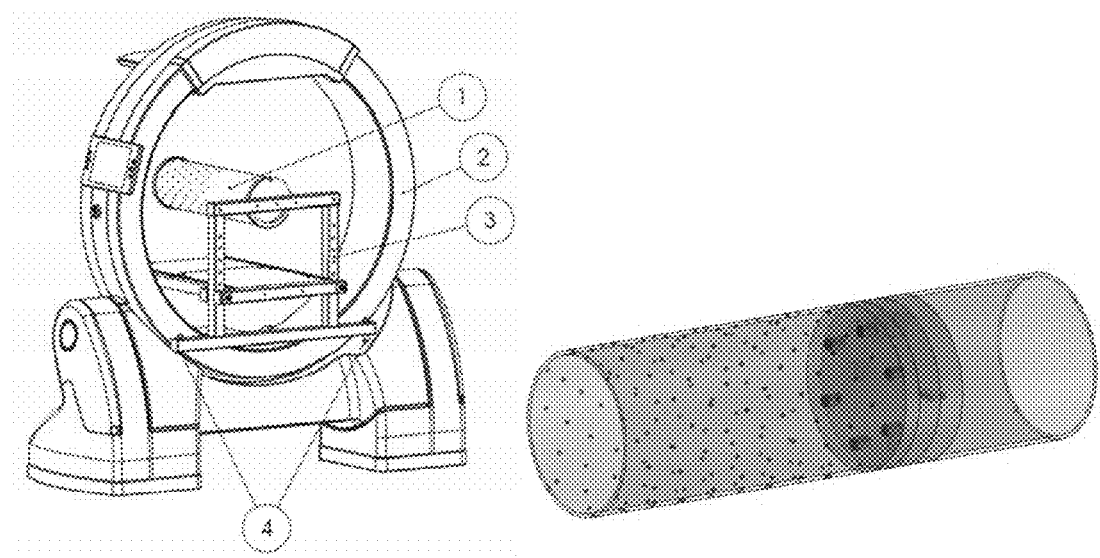

FIG. 46 shows a cylinder phantom that may be used for calibration of the system and quality assurance (QA). The left figure shows a radiotransparent plastic tube 1 with a plurality of steel balls of known 3D coordinates, a ring gantry 2, a rigid phantom holder 3 to support a mini table for positioning of QA phantoms in a ring coordinate system, and docking points 4 on a supporting structure. The right figure shows a plexi tube with marker balls (steel) and inhomogeneity inserts for system calibration and QA. X-ray images from multiple source angles are captured of the phantom, which can be reproducibly aligned with the center of the ring gantry, in order to derive gravitationally induced bending and flex of system in all degrees of freedom: source translation and tilt of central axis of collimation, detector plane rotation and tilt, for highest spatial resolution of reconstructed volumes in 3D.

Figure 47:
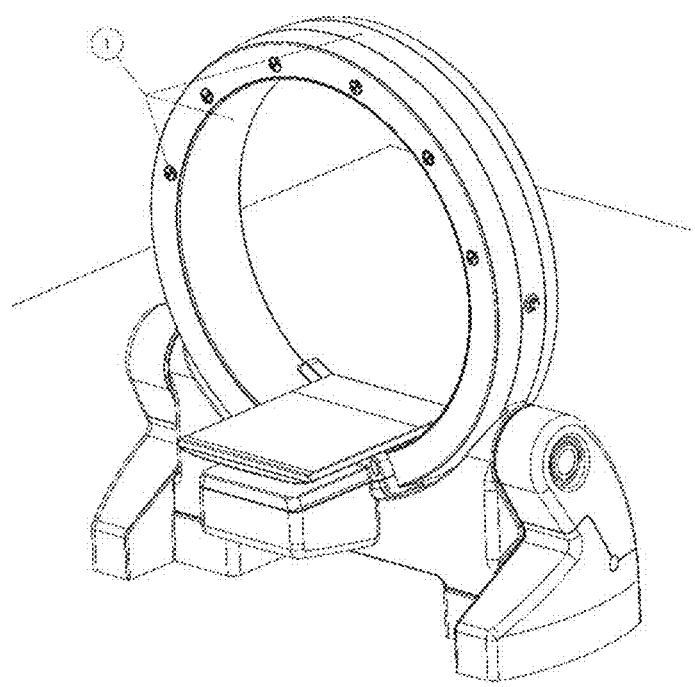

FIG. 47 shows a system of the invention including external tracking cam marker interfaces, the figure showing non rotating, stationary, rigid surfaces 1 on the ring gantry sufficient to attach markers for optical (infrared) or electromagnetic tracking of the gantry from external tracking systems in a world coordinate system. If the gantry is translated, rotated, and/or tilted, it still defines the coordinate system for the imaging components which can be registered to external (third party) systems' coordinate systems by means of tracking, e.g. in radiation therapy, surgical navigation or robotic surgery. Markers can be active or passive.

Figure 48:
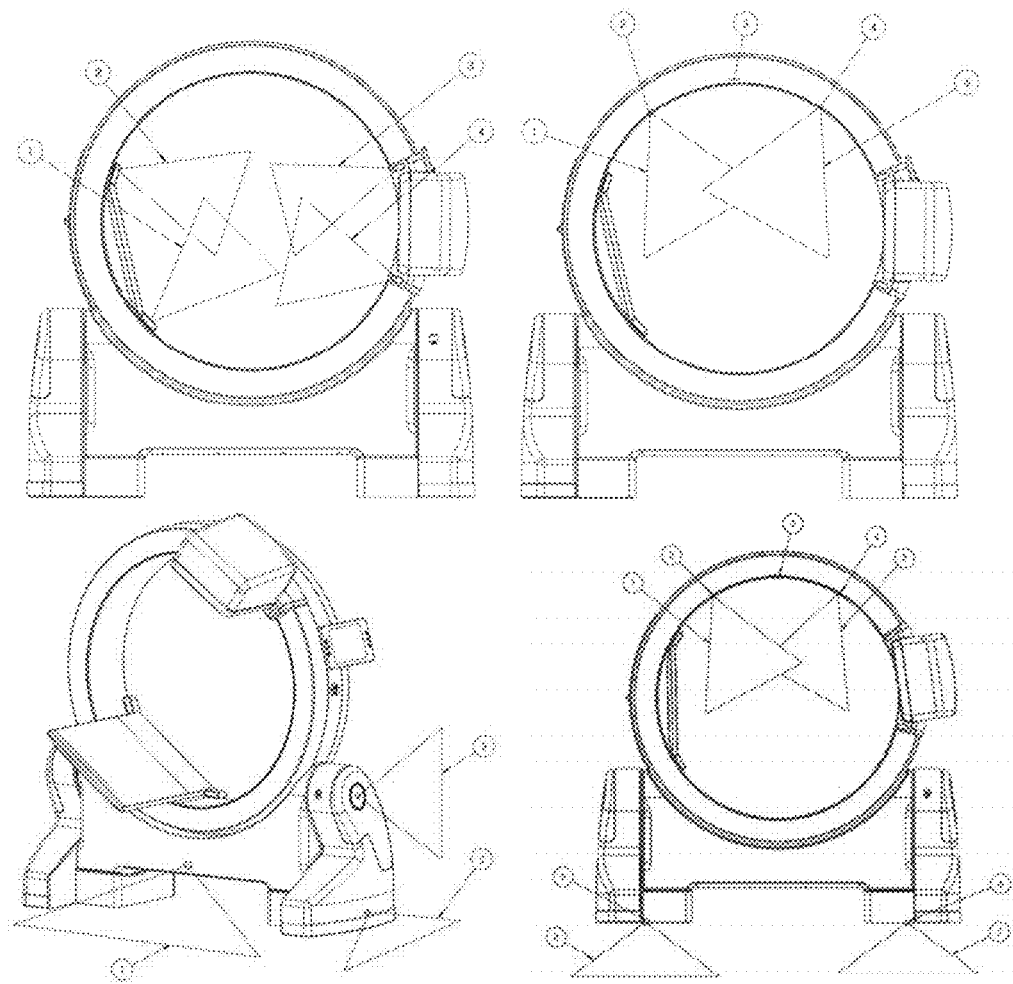

FIG. 48 shows optical FOVs of integrated (tracking) cameras. The left top figure shows symbolic FOVs of optical (stereoscopic) cameras on moving components, wherein 1 and 2 indicate the FOVs of the cameras on the detector arm, while 3 and 4 those on the source arm. The right top figure illustrates the FOV of optical (stereoscopic) cameras mounted stationary inside the ring gantry, the field of view is marked with 1 and 5, the figure showing stereoscopic cameras 1 and 4 and a video projector 3 to project structured light (for scanning applications) or information onto the skin of the patient (augmented reality applications without AR glasses for the medical team required). The left bottom figure shows cameras 1 in front and rear of the supporting structure for enhanced control during navigation of mobile unit in longitudinal direction, cameras 2 at legs, e.g. LIDAR scanners, for collision avoidance and autonomous motion in medical areas (OR, hospital), and cameras 3 for enhanced control during lateral motion. The right bottom shows additionally shows FOV of cameras 6, 9 with FOVs 7 and 8, directed towards floor, e.g. for accurate determination of system's longitudinal position during helical scans. Floor directed cameras can be combined with gantry based cameras, as those shown in the top right figure, and also the X-ray camera can be used for inter-frame registration of projection images to accurately determine the longitudinal position of single frames.

Figure 49:
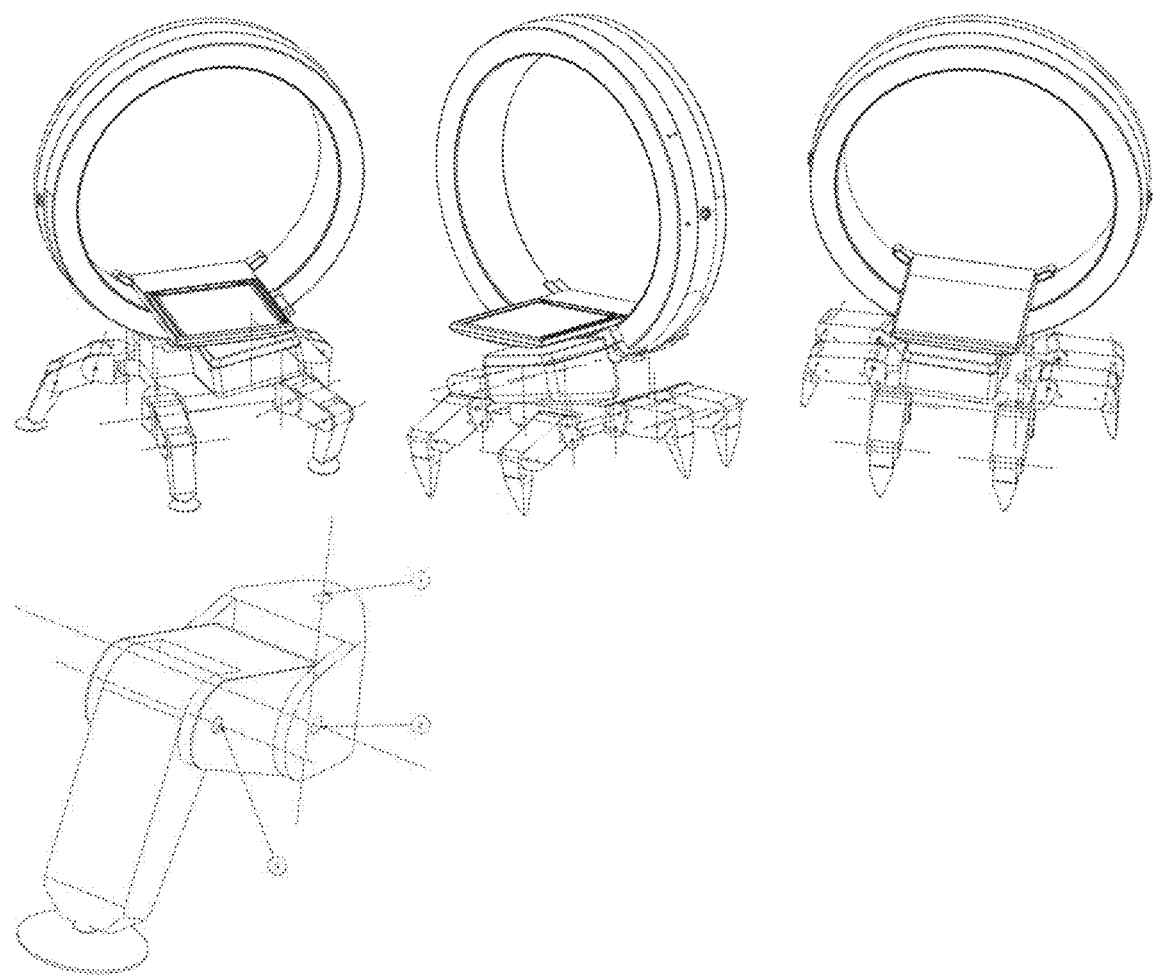

FIG. 49 exemplarily shows alternative mobility concepts. The top left shows the supporting structure for the ring gantry formed as base (platform on wheels) of a robotic quadrupod, i.e. 4 legs with 3 servos each to support the load and allow to tilt, rotate, translate and adjust the height of the gantry for imaging (helical scans can be performed without motion of wheels on floor). The top middle and right figure show a hexapod platform with 6 legs (18 servos) for improved stepping characteristics and stability. The bottom figure schematically show a leg with three joints, hip 1, knee2, and ankle 3, wherein pads (ball joints) or toes (rubber tips) are on floor.

Figure 50:
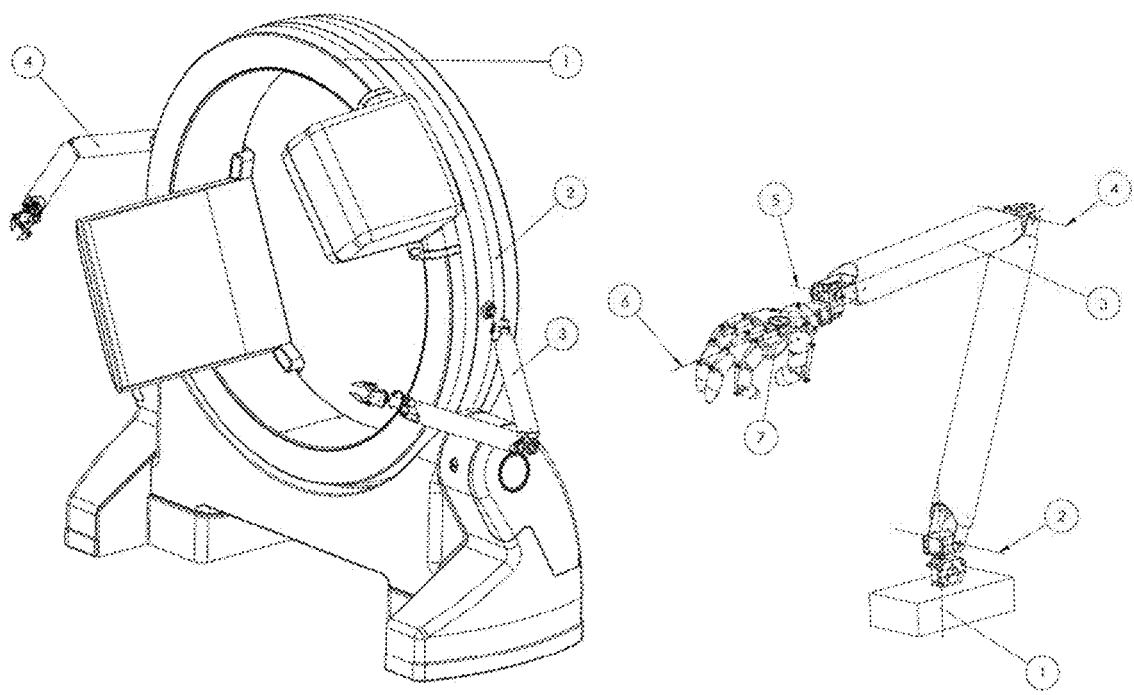

FIG. 50 illustrates the provision of additional rings. The left figure shows the source ring 1, a ring 2 for a first robotic arm, the first robotic arm 3, and a second robotic arm 4. The ring gantry cable management, bearing and drive concept is designed to accommodate multiple rings for a plurality of applications, for example, as shown, to rotate robotic arms with 6 axes to carry a tool, for example a robotic hand for usage in robotically assisted surgery or fully robotic surgery, with the advantage, that robotic motion of tools can be guided by X-ray and optical imaging on same gantry platform in one co-ordinate system. The right figure shows in more details a 6 axis robotic arm with robotic joints 1 to 6 and robotic manipulator 7. The Hand can be replaced, for example, with a sonographic ultrasound scanner, an optical surface scanner, a tool holder, claw, pliers or pincers etc.

The invention claimed is:
1. A mobile imaging ring system comprising
   a gantry shaped in a closed ring form, the gantry comprising
      an inner ring,
      a central stationary ring,
      a source ring arranged on one side of and configured to be independently rotatable along the central stationary ring, wherein a radiation source is mounted on the source ring so that the radiation source is rotatable around the gantry by rotating the source ring, and a detector ring arranged on the other side of and configured to be independently rotatable along the central stationary ring, wherein a radiation detector is mounted on the detector ring so that the radiation detector is rotatable around the gantry by rotating the detector ring, wherein the central stationary ring, the source ring and the detector ring are provided on the outer surface of the inner ring, and a supporting structure carrying the ring shaped gantry, the gantry being mounted to the supporting structure such that a plane defined by the ring shape of the gantry is tiltable relative to the supporting structure, wherein the system further comprises at least one additional rotatable ring arranged on the gantry.

2. The system of claim 1, wherein the detector and the source are mounted on the detector and source rings, respectively, such that their movements do not interfere with each other and with the supporting structure when independently rotating the detector and source rings around the entire circumference of the gantry.

3. The system of claim 1, wherein each of the rotatable detector and source rings are assembled with the stationary central ring using a ball bearing, wherein the rotatable rings preferably are gearwheel rings matching a circulating tooth belt driven by a toothed pinion on a motor.

4. The system of claim 1, wherein the source is held by a source arm mounted to the source ring, the source arm extending to one side of the gantry, and the detector is held by a detector arm mounted to the detector ring, the detector arm extending to the side of the gantry opposite to the side where the source arm extends and being folded to the inner bore of the gantry.

5. The system of claim 1, wherein the supporting structure houses a power supply such as a battery, drive controls, inverter components, a controller for signal processing, and/or a computer for image processing.

6. The system of claim 1, wherein the gantry has a generic mechanical interface and a generic electrical interface to the supporting structure.

7. The system of claim 1, wherein the electrical connection between the detector and source with electrical components housed in the supporting structure is provided via flat cables inserted into the gantry, wherein the length of the flat cables preferably corresponds at least to the circumference of the gantry in order to allow in minimum one full rotation of the detector and source rings.

8. The system of claim 1, wherein the supporting structure comprises at least two legs allowing the supporting structure to stand on the floor or being attached to a carriage on rails, each leg having a, preferably motorized, hip joint in connection with the supporting structure allowing tilting the gantry such that the plane defined by the ring shape of the gantry in a minimal range from −90° to 90° relative to the supporting structure.

9. The system of claim 1, wherein the supporting structure comprises stabilizing means for establishing a stable position of the system when standing on the floor by means of load sensors.

10. The system of claim 1, wherein the supporting structure comprises moving means for allowing a controlled movement of the system.

11. The system of claim 10, wherein the moving means comprises wheels, preferably motorized wheels, or a robotic quadrupod or hexapod.

12. The system of claim 1, wherein the system further comprises a tracking system for determining the position and orientation of the gantry relative to a room coordinate system.

13. The system of claim 1, wherein the additional ring is mounted with a robotic arm for holding additional instruments such as a sonographic sensor, a surface scanner, a second detector, a second source, a camera, a video projector, a light source, a microscope, or tools for assisting in or actively performing image guided robotic surgery or image guided radiation therapy.

14. The system of claim 1, with a movable laser system on the detector arm, comprising four independently moving and pivoting and switchable line lasers mounted on four carriages on rails parallel to the detector's active area.

15. The system of claim 1, wherein the system comprises cameras mounted to the inner ring and/or the detector arm and/or the source arm and/or the supporting structure and/or the hand held controls providing geometrical tracking information about patient, instruments and room in the ring based, mobile imaging coordinate system for navigation of instruments and/or the imaging system's moveable components.

16. The system of claim 1, further comprising a filter wheel, synchronously rotating with periodically emitted X-ray pulses from the radiation source, preferably a single source X-ray source, such that a first low energy X-ray pulse passes a first sector and a second high energy X-ray pulse passes an opposing sector on the wheel, with the filter wheel having an air insert at first sector and a beam hardening filtration at the opposing sector for enhanced dual energy imaging.

17. The system of claim 1, further comprising a filter wheel, synchronously rotating with periodically emitted X-ray pulses from the radiation source, preferably a single X-ray source, such that a first X-ray pulse passes a first sector and a second X-ray pulse passes an opposing sector on the wheel, with the filter wheel having a first sector insert comprising a plurality of concentrically aligned, ring shaped blockers with air spacers and a second sector insert comprising same plurality of circular ring shaped blockers with concentric ring shaped air spacers, whereas the second sector's rings are phase shifted such that after every first pulse is blocked and every second pulse is open for the X-ray beam for object scatter removal.

18. The system of claim 1, further comprising an anti-scatter line grid to remove object scatter from primary X-ray beams, which is movable over the active area of the radiation detector, preferably a flat panel detector in Cone Beam Computed Tomography with a sufficiently large in size to accommodate collimated fan beams to essentially perform a CT and can be retracted to perform a CBCT.

19. An independent, room mounted rail structure with adjustable inclination relative to floor with carriage and docking means to dock and move the system of claim 1 for imaging in vertical, inclined or horizontal positions.

* * * * *